US007863240B2

(12) United States Patent
Ilan et al.

(10) Patent No.: US 7,863,240 B2
(45) Date of Patent: Jan. 4, 2011

(54) METHODS AND USES OF LEPTIN IN HEPATOCELLULAR CARCINOMA

(75) Inventors: Yaron Ilan, Givat Massua (IL); Eran Elinav, Ramat Beit Hakerem (IL)

(73) Assignee: Enzo Therapeutics, Inc., Farmingdale, NY (US)

( * ) Notice: Subject to any disclaimer, the term of this patent is extended or adjusted under 35 U.S.C. 154(b) by 683 days.

(21) Appl. No.: 10/961,861

(22) Filed: Oct. 8, 2004

(65) Prior Publication Data

US 2006/0079442 A1     Apr. 13, 2006

(51) Int. Cl.
*A61K 38/00* (2006.01)
*A61K 39/00* (2006.01)
(52) U.S. Cl. .......................... 514/12; 514/21; 424/185.1
(58) Field of Classification Search ........................ None
See application file for complete search history.

(56) References Cited

U.S. PATENT DOCUMENTS 7,109,159 B1 * 9/2006 Barkan et al. .................. 514/2
2005/0176787 A1 * 8/2005 Bauer et al. .................. 514/369

FOREIGN PATENT DOCUMENTS

WO             99/40946 A2     8/1999

OTHER PUBLICATIONS

Bowie et al, 1990, Science 247:1306-1310.*
Wells, 1990, Biochemistry 29:8509-8517.*
Ngo et al., 1994, The Protein Folding Problem and Tertiary Structure Prediction, Merz et al., eds, Birkhauser, Boston, pp. 433-506.*
Bernotienne et al. (2006. Arthritis Research and Therapy. 8:217.*
Wang et al. 2004. World J Gastroenterology 10:2478-2481.*
Somasundar et al. 2004. Journal of Surgical Research 116:337-349.*
Lago et al. 2008. Cellular Immunol. 252:139-145.*
Citron et al. 2003. J Clin Oncol. 21:1-9.*
Grasso et al., "In Vivo Effects of Leptin-Related Synthetic Peptides on Body Weight and Food Intake in Female ob/ob Mice: Localization of Leptin Activity to Domains Between Amino Acid Residues 106-140", Endocrinology, 1997, pp. 1413-1418, vol. 138, No. 4, U.S.A.
Hu et al., "Leptin—A Growth Factor in Normal and Malignant Breast Cells and for Normal Mammary Gland Development", Journal of the National Cancer Institute, Nov. 20, 2002, pp. 1704-1711, vol. 94, No. 22.
Laud et al., "Identification of leptin receptors in human breast cancer: functional activity in the T47-D breast cancer cell line", Molecular and Cellular Endocrinology, 2002, pp. 219-226, vol. 188, Elsevier Science Ireland Ltd.
Muller et al., "Leptin Impairs Metabolic Actions of Insulin in Isolated Rat Adipocytes", The Journal of Biological Chemistry, Apr. 18, 1997, pp. 10585-10593, vol. 272, No. 16, U.S.A.
Okumura et al., "Leptin and high glucose stimulate cell proliferation in MCF-7 human breast cancer cells: reciprocal involvement of PKC-a and PPAR expression", Biochimica et Biophysica Acta, 2002, pp. 107-116, vol. 1592, Elsevier Science B.V.

Saxena et al., "Concomitant Activation of the JAK/STAT, PI3K/AKT, and ERK Signaling is Involved in Leptin-Mediated Promotion of Invasion and Migration of Hepatocellular Carcinoma Cells", Cancer Research, Mar. 15, 2007, pp. 2497-2507, vol. 67, No. 6.
Soma et al., "Leptin Augments Proliferation of Breast Cancer Cells via Transactivation of HER2", Journal of Surgical Research, 2007, pp. 9-14, vol. 149, Elsevier Inc.
Szanto et al., "Selective interaction between leptin and insulin signaling pathways in a hepatic cell line", PNAS, Feb. 29, 2000, pp. 2355-2360, vol. 97, No. 5.
Yin et al., "Molecular Mechanisms Involved in the Growth Stimulation of Breast Cancer Cells by Leptin", Cancer Research, Aug. 15, 2004, pp. 5870-5875, vol. 64.
Sarraf et al., "Multiple Cytokines and Acute Inflammation Raise Mouse Leptin Levels: Potential Role in Inflammatory Anorexia", The Journal of Experimental Medicine, Jan. 6, 1997, pp. 171-175, vol. 185, No. 1.
Slieker et al., "Regulation of Expression of ob mRNA and Protein by Glucocorticoids and cAMP", The Journal of Biological Chemistry, Mar. 8, 1996, pp. 5301-5304, vol. 271, No. 10, U.S.A.
de Vos et al., "Induction of ob Gene Expression by Corticosteroids is Accompanied of Body Weight Loss and Reduced Food Intake", The Journal of Biological Chemistry, Jul. 7, 1995, pp. 15958-15961, vol. 270, No. 27, U.S.A.
Chen et al., "Leptin induces proliferation and anti-apoptosis in human hepatocarcinoma cells by up-regulating cyclin D1 and down-regulating Bax via a Janus kinase 2-linked pathway", Endocrine-Related Cancer, 2007, pp. 513-529, vol. 14.
Dieudonne et al., "Leptin medicates a proliferative response in human MCF7 breast cancer cells", Biochemical and Biophysical Research Communication, 2002, pp. 622-628, vol. 293, Elsevier Science.
Garofalo et al., "Leptin Interferes with the Effects of the Antiestrogen ICI 182,780 in MCF-7 Breast Cancer Cells", Clinical Cancer Research, Oct. 1, 2004, pp. 6466-6475, vol. 10.
Grasso et al., "Inhibitory Effects of Leptin-Related Synthetic Peptide 116-130 on Food Intake and Body Weight Gain in Female C57BL/6J ob/ob Mice May Not Be Mediated by Peptide Activation of the Long Isoform of the Leptin Receptor", Diabetes, Nov. 1999, pp. 2204-2209, vol. 98.

(Continued)

*Primary Examiner*—Shulamith H. Shafer
(74) *Attorney, Agent, or Firm*—Natalie Bogdanos, Esq.; Kellie L. Carden, Esq.

(57) ABSTRACT

The present invention relates to methods for the modulation of immune responses. More particularly, the invention relates to methods and uses of leptin for immuno-modulation of the balance between the Th1/Th2 responses and for the treatment of immune-related disorders. Specifically, the methods of the invention comprise shifting the Th1/Th2 cell balance towards the proinflammatory state. This modulation of the cell balance may be performed by increasing the activity and/or the expression of leptin in said subject, for instance by raising the amount of leptin. The amount of leptin in a subject may be increased by activating immunoregulatory cells, administering an immunomodulatory amount of leptin or a homologue, derivative, or functional fragment of leptin.

4 Claims, 16 Drawing Sheets

OTHER PUBLICATIONS

Rozhavskaya-Arena et al., "Design of Synthetic Leptin Agonist: Effects on Energy Balance, Glucose Homeostasis, and Thermoregulation", Endocrinology, 2000, pp. 2501-2507, vol. 141, No. 7, U.S.A.

Faggioni et al., "IL-IB mediates leptin induction during inflammation", Am J Physiol Regulatory Integrative Comp Physiol, 1998, pp. 204-208, vol. 274.

Wang et al., "A nutrient-sensing pathway regulates leptin gene expression in muscle and fat", Nature, Jun. 18, 1998, pp. 684-688, vol. 393, No. 6686.

Lee et al., "The effects of age on uptake, serum half-life and bioavailability of mouse [D-Leu-4]OB3, a synthetic peptide amine with leptine-like activity, in male C57BL/6J mice", Regul Pept, Oct. 9, 2008, pp. 1-3, vol. 150.

Cohen et al., "Modulation of Insulin Activities by Leptin", Science Magazine, Nov. 15, 1996, pp. 1185-1188, vol. 274, No. 5290.

Zhang et al., "Crystal structure of the obese protein leptin-E100", Nature, May 8, 1997, pp. 206-209, vol. 387, No. 6629.

* cited by examiner

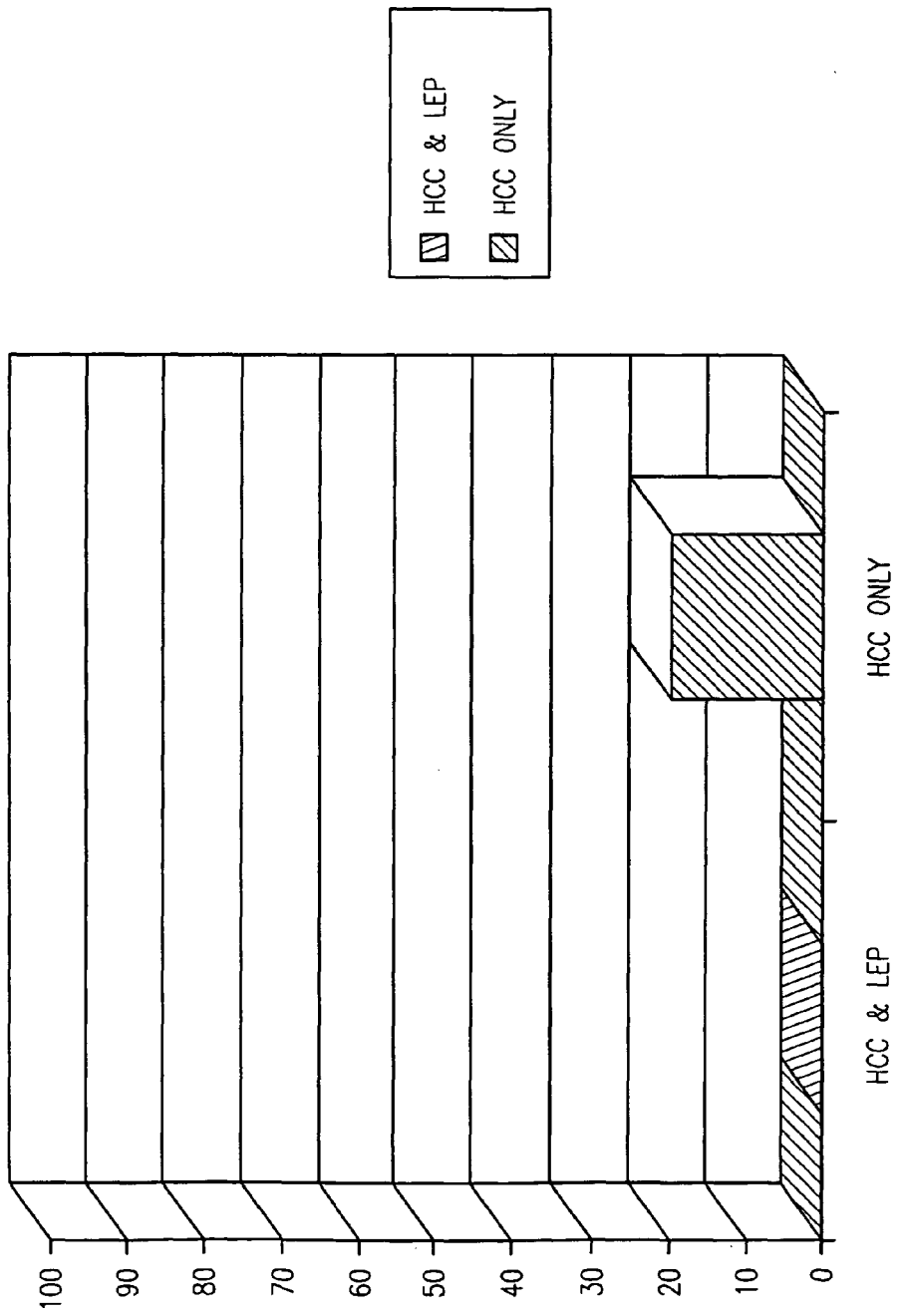

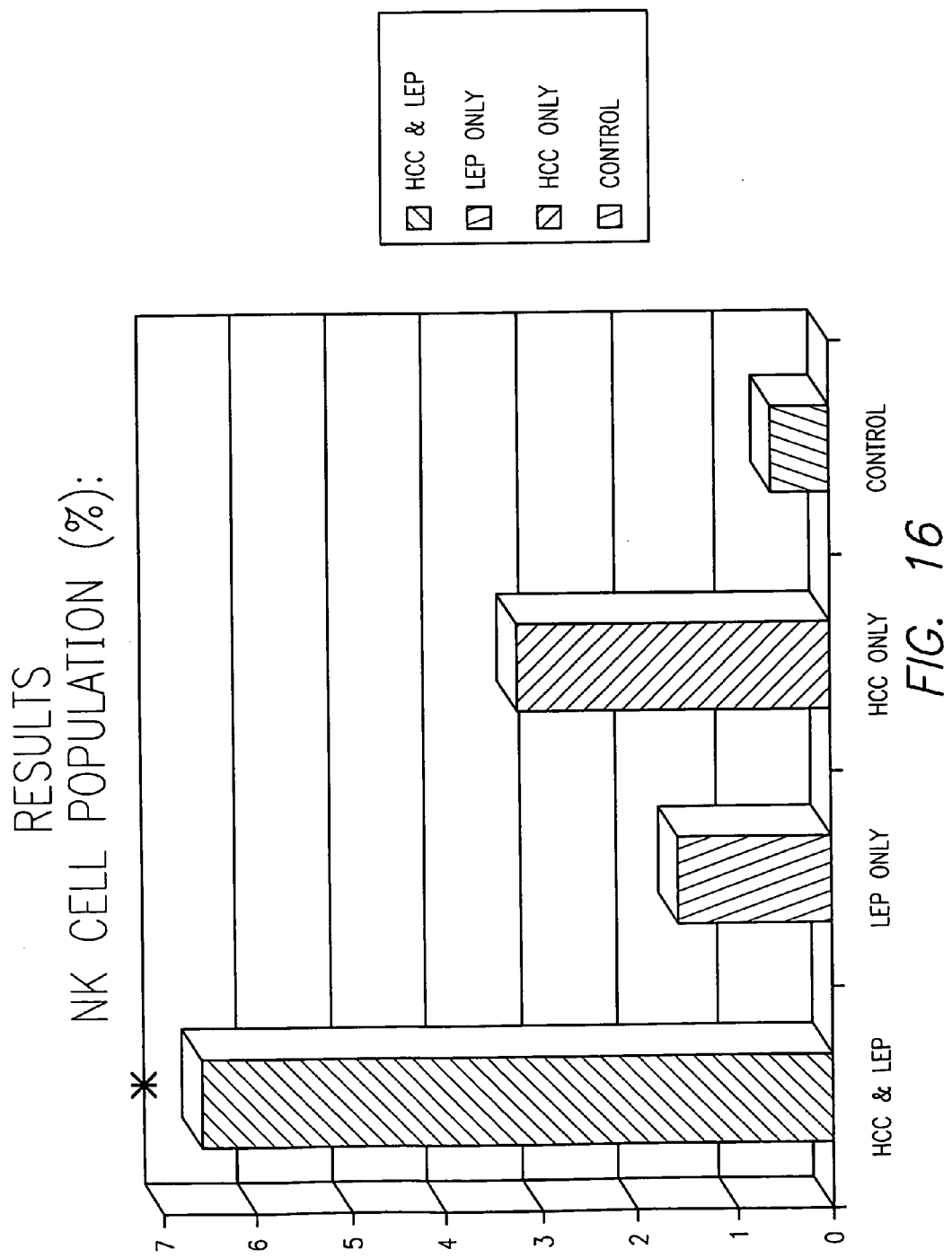

METHODS AND USES OF LEPTIN IN HEPATOCELLULAR CARCINOMA

FIELD OF THE INVENTION

The present invention relates to methods for modulation of immune response. More particularly, the invention relates to methods and uses of leptin for immuno-modulation of the balance between Th1-Th2 responses and for the treatment of immune-related disorders.

BACKGROUND OF THE INVENTION

The immune system plays a major part in tumor pathogenesis. In animal models and in humans it has been demonstrated that tumor cell formation leads to T cell activation aimed at tumor cell destruction, while the development of cancer is related to specific tumor-specific anergy. Conditions of immunodeficiency, such as infection with HIV and prolonged immunosuppressive therapy are associated with an increased incidence of cancer formation. Current anti-cancer immune therapies are aimed at correcting immune derangements in malignancy-harboring hosts. Several experimental and clinical immunomodulatory strategies are employed to activate an anti-tumor pro-inflammatory immune response in systemically disseminated tumors. Examples are numerous and include IL2 and IFN-α treatment in metastatic melanoma [Eigentler, T. K. et al., Lancet Oncol. 4(12):748-59 (2003)], IFN treatment in metastatic renal cell carcinoma [Gitlitz, B. J. and Figlin, R. A. Urol. Clin. North. Am. 30(3):589-600 (2003)], TNF-α therapy in metastatic thyroid carcinoma [Mitsiades, C. S. et al., Endocrinol. 178(2):205-16 (2003)], the use of granulocyte-colony-stimulating-factor (GCSF) as a dendritic cell activator in breast, prostate, and renal cancer [Waller, E. K. and Ernstoff, M. S. Cancer 1; 97(7):1797-809 (2003)], and transfer of alloreactive donor T lymphocytes to promote the 'graft versus leukemia' effect in hematological malignancies [Costello, R. T., et al., Eur. J. Haematol. 70(5): 333-45 (2003)].

Leptin is an 16 kDa product of the ob gene that was discovered in 1994 [Zhang, Y. et al., Nature 372:425-432 (1994)]. This protein is secreted almost exclusively by adipose cells, and acts centrally at the hypothalamic region in regulating energy expenditure and appetite [Pelleymounter, M. A. et al., Science 269:540-543 (1995)]. Leptin deficient ob/ob mice suffer from morbid obesity, diabetes mellitus, hyperlipidemia and hepatic steatosis, while leptin administration to these mice results in reversal of these disorders [Halaas, J. L. et al.,. Science 269:543-546 (1995)]. In contrast, the administration of leptin to humans suffering from morbid obesity failed to suppress appetite or reduce weight [Friedman, J. M. et al., Nutr. Rev. 60(10 Pt 2):S1-14; discussion S68-84, 85-7 (2002)]. This disappointing result may stem from increased leptin levels in obese individuals, and 'leptin resistance' caused by other, newly discovered, regulatory proteins such as adiponectin [Mark, A. L. et al., J. Hypertens. 20(7):1245-50 (2002); Berg, A. I {. et aT., Trends Endocrinol. Metab. 13(2):84-9 (2002)].

It has been previously suggested that leptin possesses potent immunomodulatory properties [Loffreda, S. et al, 12(1):57-65 (1998)]. Structurally, leptin is similar to IL2, IL6, and IL15, making it a member of the helical cytokine superfamily [Madej, T. et al., FEBS Lett. 2;373(1):13-8 (1995)], while leptin receptors are structurally similar to hematopoietic cytokine receptors [Gimble, J. M. et al., Bone 19(5):421-8 (1996)]. Leptin receptors are found on CD4 and CD8 lymphocytes, monocytes [Sanchez-Margalet, V. Clin. Exp. Immunol. 129(1):119-24 (2002)], natural-killer lymphocytes [Zhao, Y. et al., Biochem. Biophys. Res. Commun. 10:300(2):247-52 (2003); Motivala, S. J. et at., Alcohol. Clin. Exp. Res. 27(11):1819-24 (2003)], and hepatic stellate cells [Saxena, N. K. et al., Hepatology 35(4):762-71 (2002)]. Leptin enhances T cell proliferation and pro-inflammatory cytokine secretion [Lord, G. M. et al., Nature 27;394(6696):897-901 (1998); Lord, G. M. et al., J. Leukoc. Biol. 72(2):330-8 (2002); Martin-Romero, C. et al., Cell. Immunol. 10;199(1): 15-24 (2000)], by activating the JAK/STAT signal transduction pathway [Cao, Q. et al., J. Biol. Chem. 6;279(6):4292-304 (2004)]. Leptin deficient ob/ob mice are immune deficient, suffering from an increased propensity for infection and mortality [Faggioni, R. et at., FASEB J. 15(14):2565-71 (2001)] and impaired function of NKT lymphocytes and hepatic macrophages [Li, Z. et al., Gastroenterology 123(4): 1304-10 (2002)]. These mice are resistant to several Th1 mediated immune disorders, including allergic experimental encephalomyelitis [Matarese, G. et al., J. Immunol. 15;166 (10):5909-16 (2001)], concanavalin A hepatitis [Siegmund, B. et al., Eur. J. Immunol. 32(2):552-60 (2002)], experimental arthritis [Busso, N. et al., J. Immunol. 15;168(2):875-82 (2002)], and autoimmune nephritis [Tarzi, R. M. et al., Am. J. Pathol. 164(2):385-90 (2004)] but are extremely vulnerable to LPS-induced hepatic damage [Yang, S. et al., Am. J. Physiol. Gastrointest. Liver Physiol. 281(2):G382-92 (2001)]. Leptin replenishment reverses all of these effects.

Wildtype mice that do not suffer from leptin deficiency develop a potentiation in severity of experimental allergic encephalomyelitis [Matarese, G. et al., Eur. J. Immunol. 31(5):1324-32 (2001)] and type I diabetes mellitus [Matarese, G. et al. Diabetes 51(5):1356-61. (2002)]. In humans, no trials have examined the relationship between leptin and immune phenomena. However, the elevated leptin levels among females (that also suffer from an unexplained increased tendency for the development of autoimmune disease) and the reduced levels of leptin among malnourished individuals (that also tend to develop secondary immune deficiency) may point out to leptin being a link between nutrition and immunity [Matarese, G. et al., Trends in immunology. 23(4):182-7 (2002)].

Aberrant leptin receptors have been found on breast [Hu, X. et al., J. Natl. Cancer. Inst. 20;94(22):1704-11 (2002)], endometrial [Yuan, S. S. et al., Gynecol. Oncol. 92(3):769-75 (2004)], bladder [Yuan, S. S. et al., Urology. 63(2):408-13 (2004)], and esophageal [Somasundar, P. et al., Am. J. Surg. 186(5):575-8 (2003)] cancer cell lines. Leptin has been recently demonstrated to activate proliferation of breast [Catalano, S. et al., S. Biol. Chem. 25 (2004)], prostate [Onuma, M. et al., J. Biol. Chem. 24:278(43):42660-7 (2003)], and colon [Rouet-Benzineb, P. et al., S. Blot. Chem. 29 (2004)] cancer cell lines through direct activation of the JAK/STAT signal transduction pathway. In contrast, leptin was shown to inhibit proliferation of pancreatic [Somasundar P, McFadden D W, Hileman S M, Vona-Davis L. Leptin is a growth factor in cancer. J Surg Res. 2004; 116(2):337-49] and colon [Aparicio T, Guilmeau S, Goiot H, Tsocas A, Laigneau J P, Bado A, sobhani I, Lehy T. Leptin reduces the development of the initial precancerous lesions induced by azoxymethane in the rat colonic mucosa. Gastroenterology. 2004; 126(2):499-510]. While leptin levels were shown to be low in patients with gastrointestinal [Dulger H, Alici S, Sekeroglu M R, Erkog R, Ozbek H, Noyan T, Yavuz M. Serum levels of leptin and proinflammatory cytokines in patients with gastrointestinal cancer. Int J Clin Pract. 2004;58(6):545-9] [Bolukbas F F, Kilic H, Bolukbas C, Gumus M, Horoz M, Turhal N S, Kavakli B. Serum leptin concentration and advanced gastrointestinal cancers: a case controlled study. BMC Cancer. 2004;4(1):29] and pancreatic malignancies [Barber M D, McMillan D C, Wallace A M, Ross J A, Preston T, Fearon K C. The response of leptin, interleukin-6 and fat oxidation to feeding in weight-losing patients with pancreatic cancer. Br J Cancer. 2004;90(6): 1129-32], they were normal in patients with breast cancer [Stattin P, Soderberg S, Biessy C, Lenner P, Hallmans G, Kaaks R, Olsson T. Plasma leptin and breast cancer risk: a prospective study in northern Sweden. Breast Cancer Res Treat. 2004;86(3):191-6], high in patients with colorectal cancer [Stattin P, Palmqvist R, Soderberg S, Biessy C, Ardnor B, Hallmans G, Kaaks R, Olsson T. Plasma leptin and colorectal cancer risk: a prospective study in Northern Sweden. Oncol Rep. 2003;10(6):2015-21], and variable in patients receiving chemotherapy for hematological malignancy [Minami R, Muta K, Ilseung C, Matsushima T, Abe Y, Nishimura J, Nawata H. Plasma leptin levels vary with the periods during chemotherapy. Am J Hematol. 2003; 74(2): 145]. Leptin may exert two opposing effects—a direct, pro-proliferative effect on tumor cells and an indirect, pro-inflammatory and anti-tumoral immune response. The net balance between these two leptin-induced reactions may determine whether it may play a pro or anti tumorogenic effect.

The present invention shows a clear involvement of leptin in modutation of Th1 immune response, and pro-inflammatory cytokine secretion, particularly through NKT lymphocyte activation. Such modulation enables the use of leptin as an immunomodulator for the treatment of different immune-related disorders, particularly, disorders involving NK cells.

It is therefore an object of the invention to provide a method for the modulation of Th1-Th2 response, and more particularly to enhance a pro-inflammatory cytokine secretion.

Another object of the invention is to provide method for the treatment immune-related disorders by modulating the expression of leptin.

The invention further provides for the use of leptin in the treatment of immune-related disorders and in immuno-modulation.

These and other objects of the invention will become apparent as the description proceeds.

SUMMARY OF THE INVENTION

In a first aspect, the present invention relates to a method for immuno-modulation of the Th1/Th2 cell balance, in a subject in need thereof, comprising the step of modulating the levels, the expression and/or the activity of leptin in said subject.

According to one embodiment, modulation of the Th1/Th2 cell balance by the method of the invention may be performed by increasing or decreasing the levels, the activity and/or the expression of leptin in said subject.

According to another preferred embodiment, modulation of the Th1/Th2 cell balance may be mediated by the activation of immuno-regulatory cells selected from the group consisting of NK T cells, antigen presenting cells and $CD4^+$, $CD25^+$ T cells, and preferably, NK T cells, by leptin.

In one specific embodiment, the invention provides for a method for immuno-modutation resulted by the shifting of the Th1/Th2 cell balance toward the pro-inflammatory cytokine producing cells, in a subject in need thereof. Accordingly, this method comprises the step of increasing the levels, the expression and/or the activity of leptin in said subject.

More particularly, increasing the amount of leptin, the expression of leptin or leptin activity may be by carried out by a variety of means. For instance proteins or nucleic acids coding for proteins may be administered to the subject. The most obvious example of such a protein would be leptin itself, but it is also a subject of the present invention that homologues of leptin, functional derivatives of leptin or fragments of leptin may also be used if they are capable of inducing appropriate immune modulations. Another example of a protein is an anti-idiotypic antibody to leptin, since it has been previously shown that an anti-idiotypic antibody is capable of inducing the same interactions with the leptin receptor that can be seen with the leptin molecule itself [De Fanti et al., Obesity Research 10:833-837 (2002)]. Rather than using these proteins themselves, nucleic acids may be used that code for these proteins after introduction into a cell. For instance, it has been previously shown that nucleic acid constructs that express the leptin gene can induce cells to excrete leptin [MacDougald et al., Proc Nat. Acad Sci USA 92:9034-9037 (1995)]. As described previously constructs that express modified versions or portions of the leptin gene may also be used. Furthermore, there are small molecules that have been described in the literature among whose properties include the ability of raising the level or activity of leptin in a subject. For instance, thiazolidinedione, a drug that is used to treat diabetes, has the effect of raising leptin levels but it has been disclosed in U.S. patent application Ser. No. 20020032225 that diphenylethylene compounds that contain either thiazolidinedione moieties or a related drug, oxazolidinedione have the opposite effect and raises leptin levels. Another example is nicotinic acid and nicotinic acid esters which have also been shown to increase the amount of leptin in a subject [U.S. patent application Ser. No. 20020128298]. It should be noted that it is a subject of the present invention that these reagents may be used alone or they may be used in various combinations.

According to a specifically preferred embodiment, the method of the invention is particularly useful for shifting of the Th1/Th2 cell balance toward the pro-inflammatory cytokine producing cells a mammalian subject suffering of an immune-related disorder.

More preferably, shifting of the Th1/Th2 cell balance toward the pro-inflammatory cytokine producing cells may be particularly advantageous for immune-related disorder such as malignant proliferative disorder, a disorder caused by immuno-suppression or an infection caused by a pathogenic agent.

According to one embodiment, a malignant proliferative disorder may be any one of solid and non-solid tumors selected from the group consisting of carcinoma, sarcoma, melanoma, leukemia and lymphoma.

According to another particular embodiment, the method of the invention may be advantageous for Hepatocellular carcinoma (HCC).

In another preferred embodiment, the subject in need of modulating the Th1/Th2 cell balance toward the pro-inflammatory cytokine producing cells by the method of the invention may suffer from any immuno-suppressive disorder, for example immune suppression caused by infection of an immunodeficiency virus, preferably, HIV, or alternatively, immuno-suppression caused by chemotherapy.

According to another embodiment, shifting of the Th1/Th2 cell balance toward the pro-inflammatory cytokine producing cells by the method of the invention may be advantageous in a subject suffering of an infection, for example infection caused by a pathogenic agent selected from the group consisting of bacterial pathogens, viruses, fungi, parasites and yeast.

The invention further provides for a method for the treatment of an immune-related disorder in a subject in need thereof, comprising the step of administering to said subject an immuno-modulatory effective amount of a protein or nucleic acid that will increase the amount of leptin, the expression of leptin or leptin activity in the subject. Examples of proteins can comprise but not be limited to leptin, homologues of leptin, functional derivatives of leptin, leptin fragments and anti-idiotypic antibodies to leptins. Nucleic acids useful for the purpose of increasing the amount, expression or activity of leptin can be designed to express any of the foregoing proteins. Small molecules such as nicotinic acids, nicotinic acid ester or diphenylethylene compounds that contain either thiazolidinedione or oxazolidinedione moieties may also find use in the present invention. These compounds or reagents may be used alone or they maybe used in combination with each other.

In one embodiment, the effective amount administered to a subject suffering from an immune-related disorder may be an amount sufficient for shifting the Th1/Th2 cell balance toward pro-inflammatory cytokine producing cells.

According to another embodiment, the method of the invention is particularly applicable for the treatment of an immune-related disorder such as any one of a malignant proliferative disorder, a disorder caused by immuno-suppression or an infection caused by a pathogenic agent.

More particularly, the method of the invention is particularly applicable for the treatment of a malignant proliferative disorder such as any one of solid and non-solid tumors selected from the group consisting of carcinoma, sarcoma, melanoma, leukemia and lymphoma.

According to a specifically preferred embodiment, the method of the invention is for the treatment of Hepatocellular carcinoma (HCC).

According to another embodiment, the method of the invention is suitable for the treatment of immuno-suppression caused by infection of an immunodeficiency virus, preferably, HIV, or caused by chemotherapy.

Still further, the method of the invention is intended for the treatment of an infection caused by a pathogenic agent, for example, bacterial pathogens, viruses, fungi, parasites or yeast.

In another aspect, the invention relates to the use of a protein or nucleic acid that increases the amount, expression or activity of leptin for the preparation of a composition for shifting the Th1/Th2 cell balance toward pro-inflammatory cytokine producing cells.

The invention further relates to the use of protein or nucleic acid that increase the amount, expression or activity of leptin for the preparation of a medicament for the treatment of an immune-related disorder.

According to one embodiment of said aspect, the immune-related disorder may be any one of a malignant proliferative disorder, a disorder caused by immuno-suppression or an infection caused by a pathogenic agent.

Specifically, a malignant proliferative disorder may be any one of solid and non-solid tumors selected from the group consisting of carcinoma, preferably, Hepatocellular carcinoma (HCC), sarcoma, melanoma, leukemia and lymphoma.

In another embodiment, the immune related disorder may be immuno-suppression, for example, caused by infection of an immunodeficiency virus, preferably, HIV, or alternatively, by chemotherapy.

In yet another embodiment, the immune related disorder may be infection caused by a pathogenic agent selected from the group consisting of bacterial pathogens, viruses, fungi, parasites and yeast.

In a third aspect, the invention relates to a method for immuno-modulation of the immune system resulted by shifting the Th1/Th2 cell balance toward the anti-inflammatory cytokine producing cells, in a subject in need thereof. Such method comprises the step of decreasing the levels, the expression and/or the activity of leptin in said subject.

Decreasing the amount of leptin, the expression of leptin or the activity of leptin can be carried out by a variety of means. For instance, an immunomodulatory effective amount of proteins or nucleic acids may be administered to the subject for this purpose. Examples of proteins can comprise but not be limited to antibodies to either leptin or the leptin receptor which are obtainable from a wide variety of commercial sources. Competitors such as soluble leptin receptor [Yang et al., Molec Endricrinol 18:1354-1362 (2004)] or a fragment of Helix III of leptin [Gonzalez and Leavis, 2003 Endocrine 21:185-196 (2003)] can also result in a loss of leptin signaling. Thus it is also a subject of the present invention that fragments of the leptin or the leptin receptor may also find use with present invention. Alternatively, instead of the proteins themselves, nucleic acid constructs coding for the foregoing proteins may also be used. Furthermore, nucleic acids may be used which comprise sequences complementary to either leptin or the leptin receptor where the nucleic acids comprise antisense DNA, antisense RNA, ribozymes or small interfering RNA (siRNA) that target leptin or the leptin receptor or they may be expression constructs that direct synthesis of antisense RNA, ribozymes or siRNA. In addition to these means, other molecules may also be used that decrease the amount of leptin, the expression of leptin or the activity of leptin. Examples of these can comprise but not be limited to thiazolidinediones [Kallen and Lazar, Proc. Nat, Acad. Sci. USA 93:5793-5796 (1996)], galanin [Li et al., J Mol Endocrinol. 33:11-19 (2004)], SOCS-3 (U.S. patent application 20040087530) and the beta 3-adrenoceptor agonists BRL35135A and ZD2079 [Trayhurn et al., Biochem Biophys Res Commun 228:605-610 (1996)]. These compounds or reagents may be used alone or they maybe used in combination with each other.

According to a specific embodiment, a subject may be a mammalian subject suffering from an immune-related disorder.

More particularly, the immune-related disorder may be any one of an inflammatory disorder, an autoimmune-disorder, a graft-rejection associated disorder or a fibrotic disorder.

In one embodiment, an inflammatory disorder may be an intestinal inflammatory disease, preferably, an inflammatory bowel diseases (IBD).

In another embodiment, the immune-related disorder may be a fibrotic disorder, for example, hepatic fibrosis, cardiac fibrosis, or colon fibrosis.

In yet another embodiment, shifting the Th1/Th2 cell balance toward the anti-inflammatory cytokine producing cells, may be performed in a subject suffering from an auto-immune disease such as arthritis, diabetes or immune related infertility disorders.

The invention further provides for a method for the treatment of an immune-related disorder in a subject in need thereof. The method of the invention comprises the step of administering to said subject an immuno-modulatory effective amount of proteins or nucleic acids that will decrease the amount of leptin, the expression of leptin or leptin activity. Examples of proteins can comprise but not be limited to leptin fragments, antibodies to leptin, fragments of antibodies to leptin, soluble leptin receptor, fragments of the leptin receptor, antibodies to the leptin receptor and fragments of antibodies to leptin receptor, galanin and the SOCS-3 gene product. Examples of nucleic acids can comprise but not be limited to oligonucleotides or nucleic acids that act as antisense, ribozymes or siRNA or that code for expression of antisense RNA, ribozymes or siRNA. These compounds or reagents may be used alone or they maybe used in combination with each other.

According to one embodiment, an effective amount may be an amount sufficient for shifting the Th1/Th2 cell balance toward anti-inflammatory cytokine producing cells.

In another embodiment, the method of the invention is intended for the treatment of an immune-related disorder such as inflammatory disorder, an autoimmune-disorder a graft-rejection associated disorder or a fibrotic disorder.

According to a specific embodiment, the method of the invention is particularly advantageous for the treatment of an inflammatory disorder, preferably, an intestinal inflammatory disease or most preferably, inflammatory bowel diseases (IBD).

According to another specific embodiment, the method of the invention is suitable for the treatment of a fibrotic disorder such as any one of hepatic fibrosis, cardiac fibrosis or colon fibrosis.

Still further, the method of the invention may be applicable for the treatment of auto-immune disease, for example, any one of arthritis, diabetes or immune-related infertility disorders.

According to another aspect, the invention relates to the use of a protein or nucleic acid that can reduce the amount, expression or activity of leptin for the preparation of a composition for shifting the Th1/Th2 cell balance toward anti-inflammatory cytokine producing cells.

The invention further provides for the use of any one of a protein or nucleic acid that can reduce the amount, expression or activity of leptin for the preparation of a medicament for the treatment of an immune-related disorder.

According to one embodiment, an immune-related disorder may be any one of an inflammatory disorder, an autoimmune-disorder, a graft-rejection associated disorder or a fibrotic disorder.

More specifically, an inflammatory disorder may be an intestinal inflammatory disease, preferably, inflammatory bowel diseases (IBD).

In another embodiment, the immune related disorder may be a fibrotic disorder such as hepatic fibrosis, cardiac fibrosis or colon fibrosis.

In yet another embodiment, the immune-related disorder may be an auto-immune disease, for example, arthritis, diabetes or immune-related infertility disorders.

According to another aspect, the invention relates to a method for the treatment of immune-related disorders in a mammalian subject in need of such treatment, by manipulating NK T cell population of said subject, wherein manipulation of said NK T cell population results in modulation of the Th1/Th2 cell balance, said method comprises the steps of: (a) obtaining NK T cells from said subject; (b) ex vivo educating the NK T cells obtained in step (a) by culturing the NKT cells in the presence of (i) an antigen or antigens associated with said immune-related immune disorder; (ii) an antigen presenting cell, preferably DC and (iii) leptin, any homologue, analogue, derivative or functional fragment of leptin, an expression vector comprising a nucleic acid sequence encoding for leptin or any functional fragments thereof, a protein, a peptide, an anti-idiotype antibody to leptin, a diphenylethylene compound containing thiazolidinedione or oxazolidinedione, nicotinic acid, a nicotinic ester, an antibody specific for leptin, a fragment of an antibody to leptin, an antibody to the leptin receptor, a fragment of an antibody to the leptin receptor, soluble leptin receptor, a fragment of leptin receptor, a protein or peptide capable of inhibiting the expression of leptin, a nucleic acid or an oligonucleotide comprising sequences complementary to leptin or leptin receptor mRNA sequences, a leptin anti-sense nucleic aid sequence, a ribozyme, a small interfering RNA (siRNA) specific for leptin, a thiazolidinedione compound, galenin, SOCS-3, a beta 3-adrenoreceptor, or any combination of any of the foregoing.

The invention further provides for a therapeutic composition for the treatment of an immune-related disorder in a mammalian subject. The composition of the invention comprises as an effective ingredient ex vivo educated autologous NK T cells capable of modulating the Th1/Th2 cell balance, and optionally further comprising pharmaceutically acceptable carrier, diluent, excipient and/or additive.

Histogram showing proliferation of NKT cells isolated from experimental groups A-H. As shown by the figure, leptin induces a significant increase in in-vitro proliferation of NKT lymphocytes that are incubated with HCC-related antigens in the present of DC's.

Figures 2A, 2B:
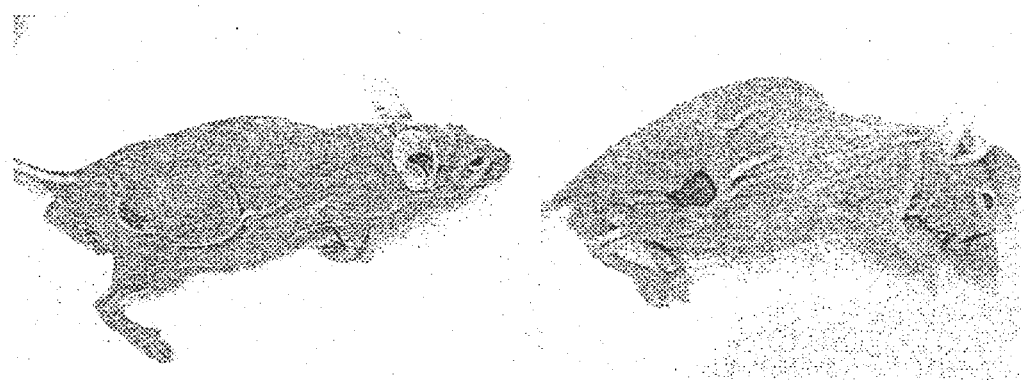

FIG. 2A-2B Leptin decrease HCC in T cell deficient nude mice

Demonstrative photograph of a mouse that was not administered leptin (FIG. 2A) five weeks after the subcutaneous implantation of hepatocellular carcinoma showing a large tumor. Mouse that was continuously administered leptin (FIG. 2B) developed a significantly smaller tumor, with a large necrotic center.

Figure 3:

FIG. 3 Leptin significantly decrease tumor size in T cell deficient nude mice

Tumors of mouse group A that was administered leptin (top row) were significantly smaller in size than tumors of mouse group C that was not administered leptin (bottom row). The latter group featured a 20% mortality, as compared to 0% in the former group.

Figures 4A, 4B:
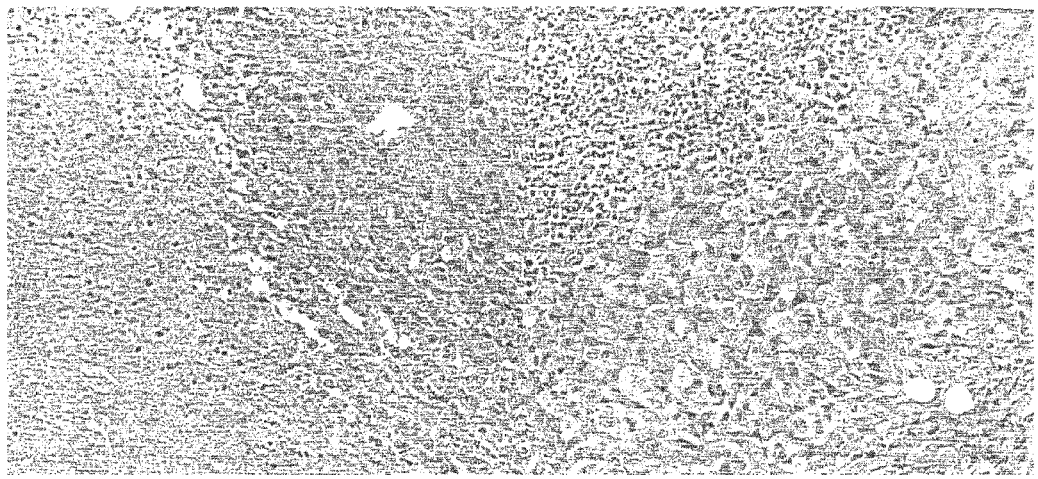

FIG. 4A-4B Leptin induces an intense inflammatory response in tumor interphase areas Histological evaluation of excised tumors of group C mice (not administered leptin) revealed a lack of inflammatory response in interphase areas (FIG. 4A). In comparison, group A mice that were administered leptin uniformly developed an intense inflammatory response in tumor interphase areas (FIG. 4B).

Figure 5:
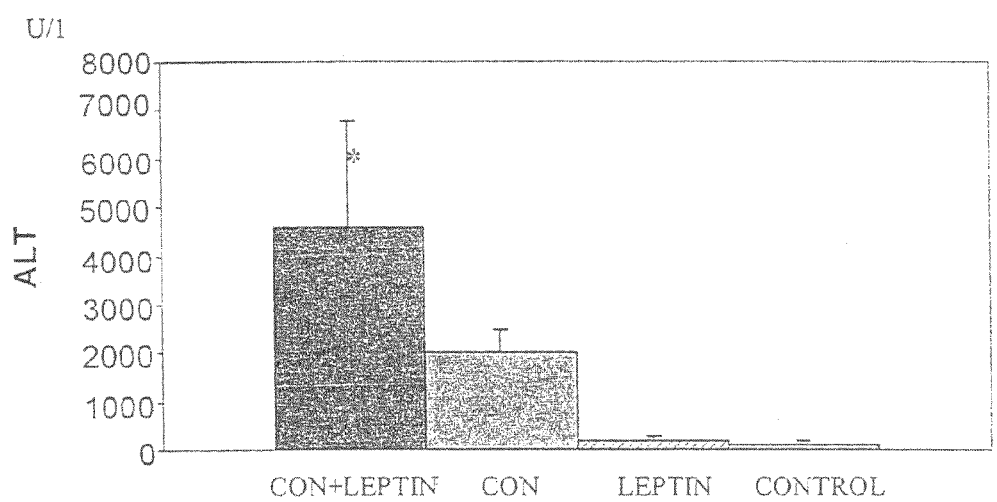

FIG. 5 Leptin induces a significant increase in serum ALT activity 8 hours following concanavalin A infusion Histogram demonstrate the ALT activity of four experimental groups, con+leptin, con, leptin and control.

Figures 6A, 6B, 6C:
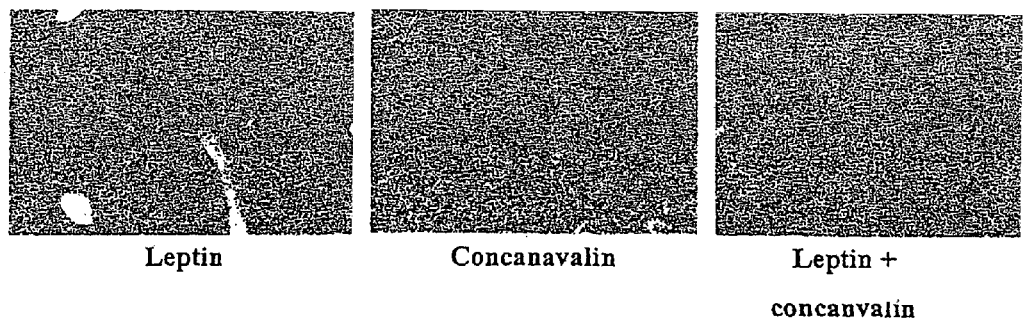

FIG. 6A-6C leptin induces a significant exacerbation of concanavalin-induced hepatitis Hepatic histological sections showing that leptin induces a significant exacerbation of concanavalin-induced hepatitis (FIG. 6C) in comparison to concanavalin alone (FIG. 6B). Leptin administration by itself did not produce any hepatic damage (FIG. 6A).

Figure 7:
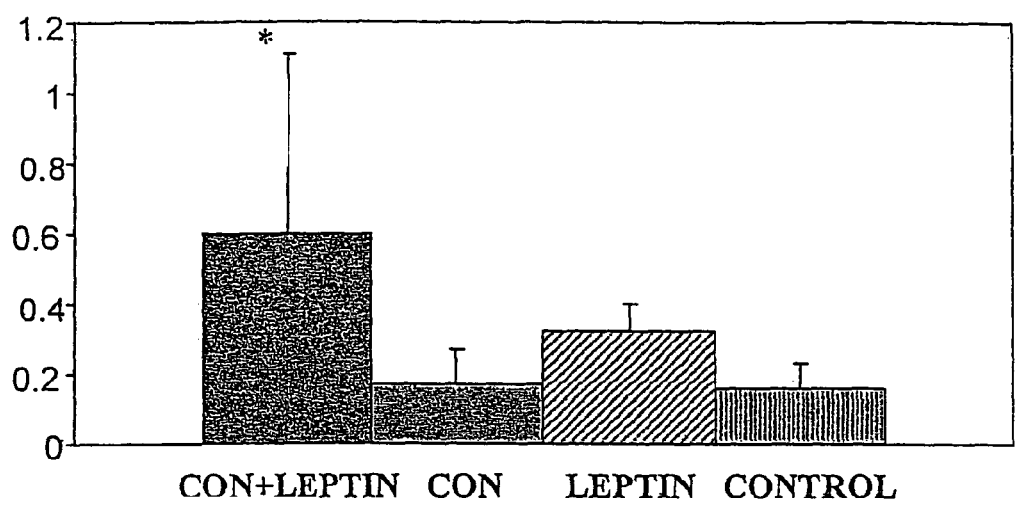

FIG. 7 Leptin significantly increases the ratio of in-vitro splenocyte secretion of IFN-γ and IL10 (IFN-γ/IL10)

Histogram showing the IFN-γ/IL10 ratio in four different experimental groups A-D including con+leptin, con, leptin and control group, respectively.

Figure 8:
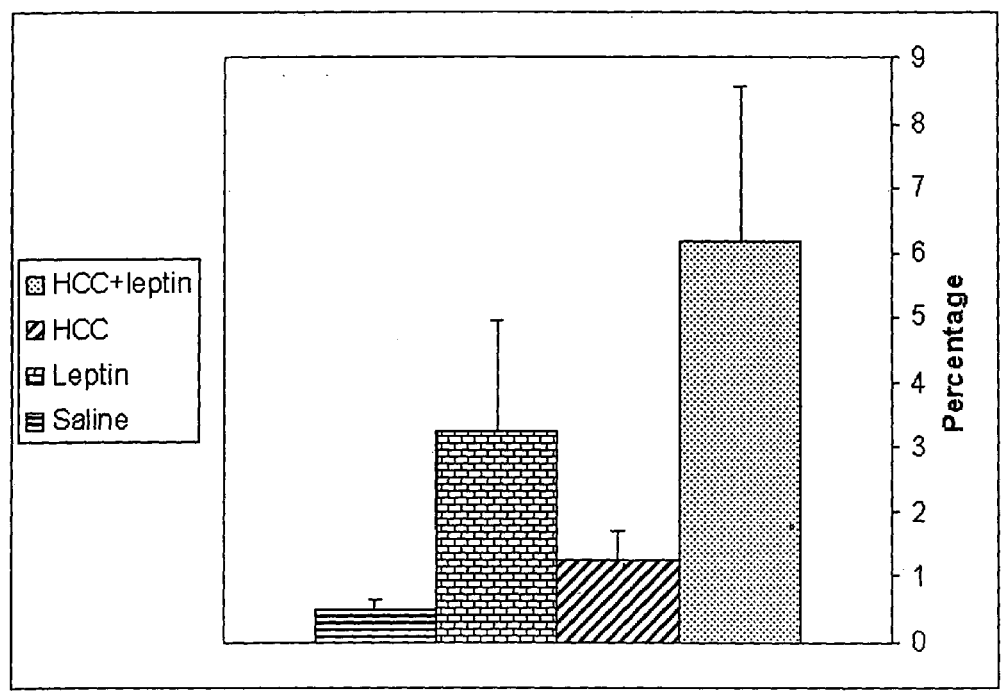

FIG. 8 Leptin increases inflammation

Figure 9:
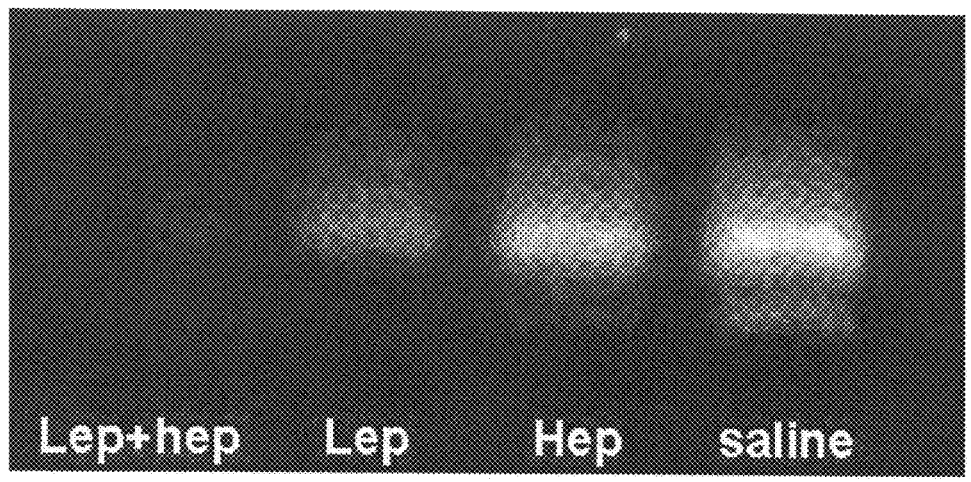

FIG. 9 rt PCR analysis of peripheral lymphocytes mRNA expression

Figure 10:
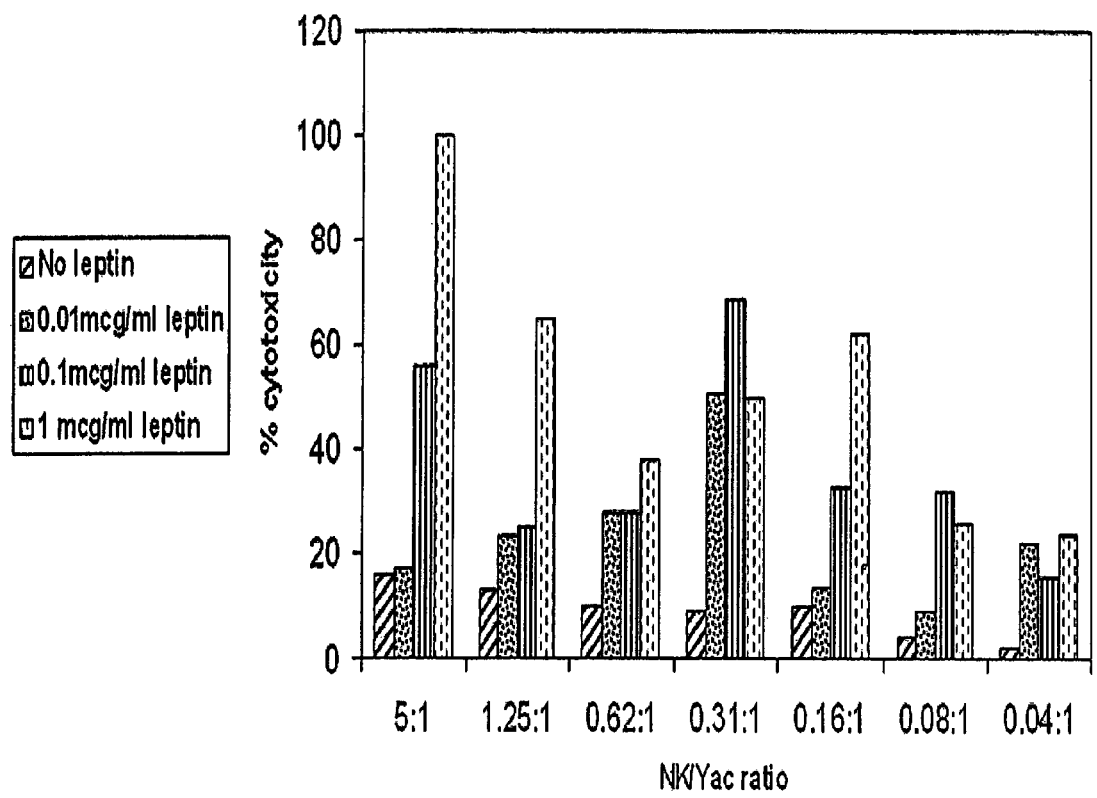

FIG. 10 Leptin increases natural killer cell cytotoxicity

Figure 11:
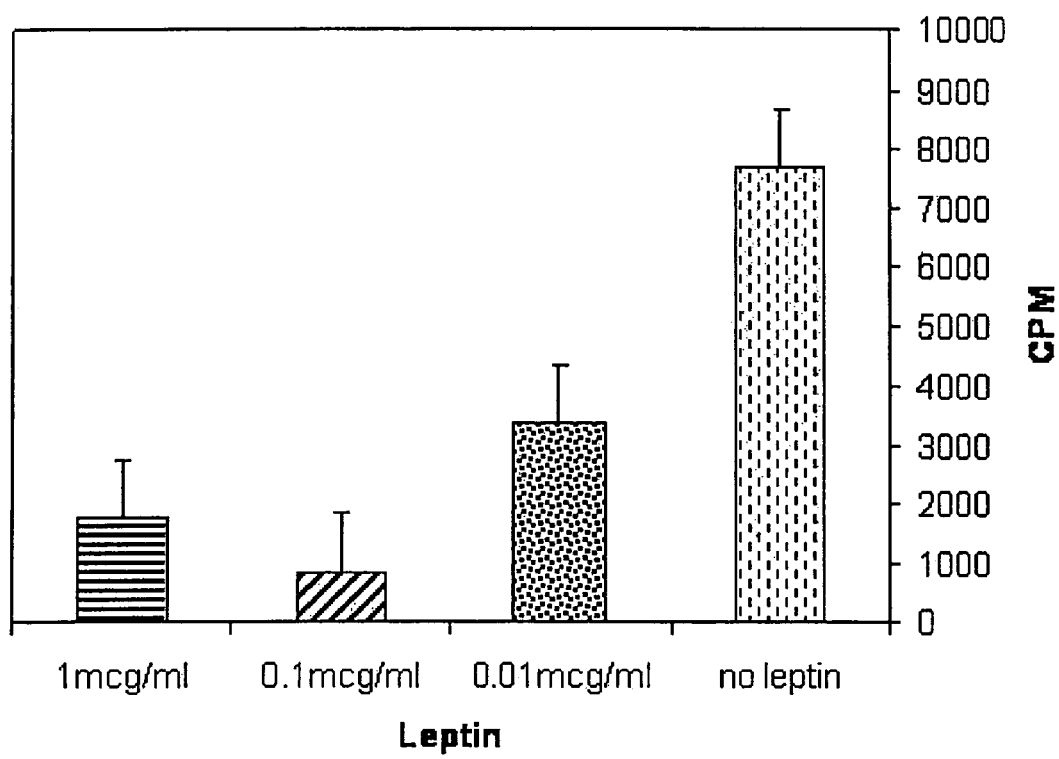

FIG. 11 Leptin inhibits tumor cell growth

Figure 12:
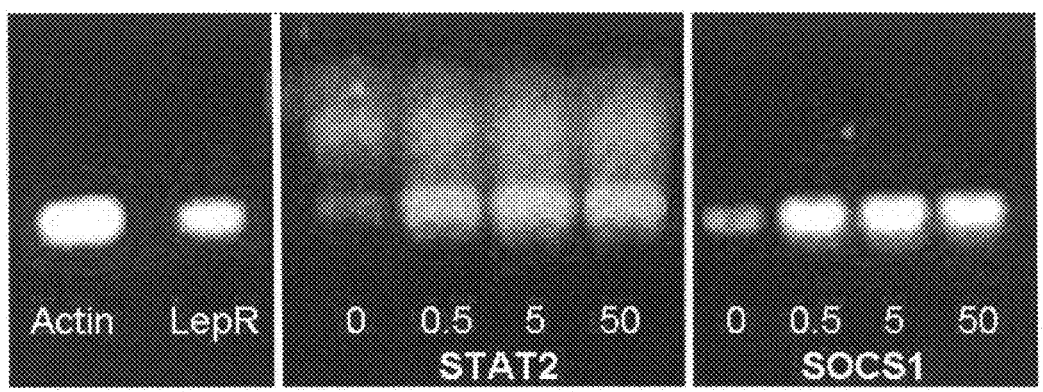

FIG. 12 rtPCR analysis of mRNA expression of STAT2 and SOCS1 in HCC cells

Figure 13:
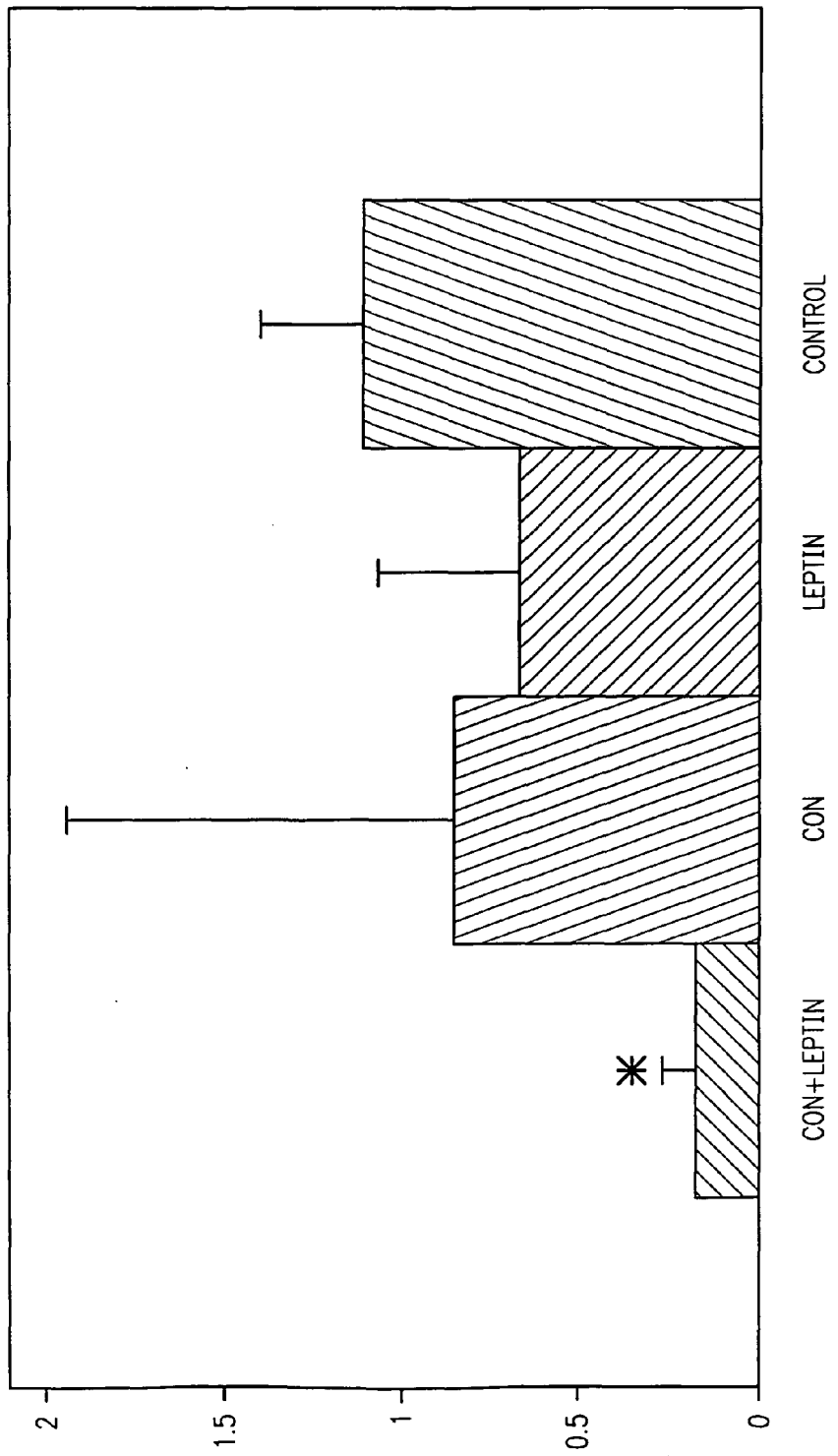

FIG. 13 Leptin decreases the hepatic/splenic NKT cell ratio. Histogram showing the NKT/lymphocyte ratio in four experimental groups A-D including con+leptin, con, leptin and control group, respectively.

Figure 14:
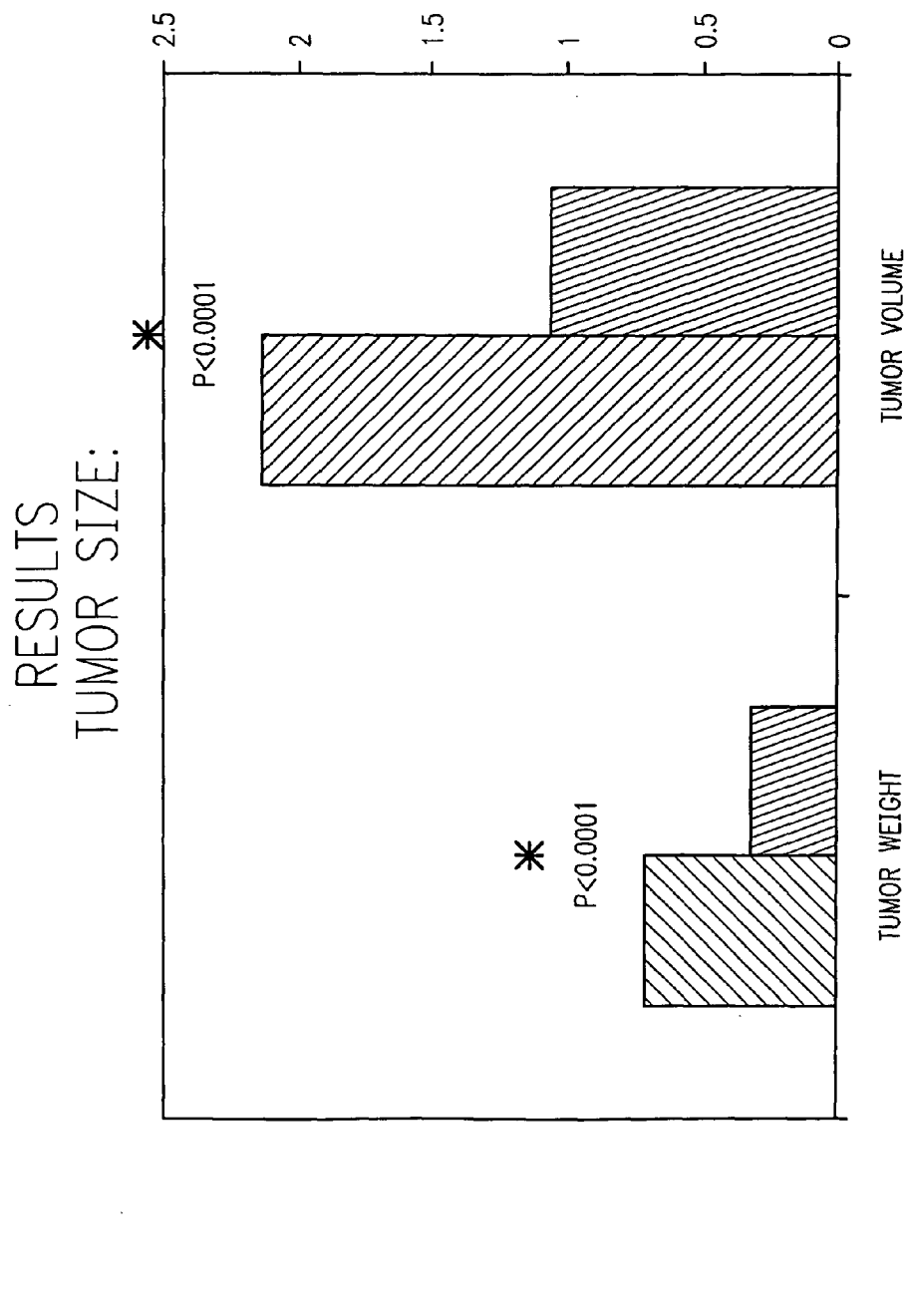

FIG. 14 Leptin significantly decreases tumor weight and volume

FIG. 15 Leptin significantly decreases Hepatocellular Carcinoma mortality

FIG. 16 Leptin increases the NK cell population

DETAILED DESCRIPTION OF THE INVENTION

A number of methods of the art of molecular biology are not detailed herein, as they are well known to the person of skill in the art. Such methods include site-directed mutagenesis, PCR cloning, expression of cDNAs, analysis of recombinant proteins or peptides, transformation of bacterial and yeast cells, transfection of mammalian cells, and the like. Textbooks describing such methods are e.g., Sambrook et al., Molecular Cloning A Laboratory Manual, Cold Spring Harbor Laboratory; ISBN: 0879693096, 1989, Current Protocols in Molecular Biology, by F. M. Ausubel, ISBN: 047150338X, John Wiley & Sons, Inc. 1988, and Short Protocols in Molecular Biology, by F. M. Ausubel et al., (eds.) 3rd ed. John Wiley & Sons; ISBN: 0471137812, 1995. These publications are incorporated herein in their entirety by reference. Furthermore, a number of immunological techniques are not in each instance described herein in detail, as they are well known to the person of skill in the art. See e.g., Current Protocols in Immunology, Coligan et al., (eds), John Wiley & Sons. Inc., New York, N.Y.

Leptin is a hormone which has been shown to interact with its cognate receptor, thereby initiating its cell-signaling pathway. Several different leptin receptor isoforms are predicted to exist, including a long form which has the highest level of expression in regions of the hypothalamus, and specific regions therein, including the arcuate nucleus and the dorsomedial hypothalamus. In vitro and in vivo studies demonstrate that leptin activates cytokine-like signal transduction by stimulating the classic JAK-STAT pathway via the long receptor isoform [Ghilardi, N. et al., Proc. Natl. Acad. Sci. USA. 93:6231-6235 (1997); Baumann, H. et al, Proc Natl. Acad. Sci. USA 93:8374-8378 (1996); Vaisse C. et al., Nature Genetics 14:95-97 (1996)]. Lack of functional leptin or of long form leptin receptors in the ob/ob and db/db mice, respectively, causes severe obesity [Zhang, et al., Nature 372: 425-432 (1994); Lee, G. H. et al., Nature 379:632-635 (1996); Chen, H. et al., Cell 84:491-495 (1996)].

The cloning of the genes encoding leptin [Zhang (1994) ibid.,] and the leptin receptor [Tartaglia, et al., 61183:1263-1271(1995)], and the study of these proteins in vivo and in vitro, have dramatically demonstrated the importance of this ligand-receptor system in the normal regulation of body weight and energy balance.

In addition to this role which has been proposed to be its primary function, circulating leptin also appears to play an important role in the neuroendocrine axis [Ahima, R. S., et al., Nature 382:250-252 (1996)], including the regulation of reproduction. Administration of exogenous leptin has been shown to induce the onset of puberty in mice [U.S. patent application Ser. No. 08/749,534, the teachings of which are incorporated herein by reference in its entirety].

The inventors have now shown that leptin is involved in immuno-modulation of the Th1/Th2 response, and particularly leads to enhancement of the pro-inflammatory response.

As shown by Example 1, leptin induces NK T cell proliferation, therefore, leptin could induce a pro-inflammatory response via NK T cells.

Thus, in a first aspect, the present invention relates to a method for immuno-modulation of the Th1/Th2 cell balance, in a subject in need thereof, comprising the step of modulating the levels, the expression and/or the activity of leptin in said subject.

According to one embodiment, modulation of the Th1/Th2 cell balance by the method of the invention may be performed by increasing or decreasing the levels, the activity and/or the expression of leptin in said subject.

As shown by the present invention leptin may act as a potent immuno-modulator by modulating the Th1/Th2 balance in a subject suffering from an immune-related disorder. However, it is to be appreciated that the modulation processes regulated by leptin may be further mediated by different components of the subject's immune system, such as cellular immune reaction elements, humoral immune reaction elements and cytokines. Therefore, leptin may play a dual role in immune modulation by switching the immune response in the immunogenic or tolerogenic directions. Thus, regulation of the immune response by leptin depends on the environment of such immune response, which is determined by different types of stimulations and different signaling pathways. It is noteworthy that leptin is involved in distinct immunoregulatory mechanisms, and modulates different types of effector cells and the Th1/Th2 paradigm in immune-mediated disorders.

According to a specific preferred embodiment, modulation of the Th1/Th2 cell balance may be mediated by the activation of immuno-regulatory cells selected from the group consisting of NK T cells, antigen presenting cells and $CD4^+$, $CD25^+$ T cells, and preferably, NK T cells, by leptin.

The findings of the invention therefore provide new modalities by using leptin as an immuno-regulator agent.

It is therefore particularly interesting to note that NK T cells, and particularly, NK1.1 T cells may be involved in keeping a balance between anti-inflammatory and pro-inflammatory lymphocytes via cytokines secretion and/or killing, and may be involved in the determination of T helper cell differentiation [Arase, H., et al., Eur. J. Immunol. 23: 307-310 (1993); Yoshimoto, T, et al., J. Exp. Med. 179:1285-1295 (1994), MacDonald, H. R., et al., J. Exp. Med. 182:633-638 (1995), Seder, R. A. et al., Annu. Rev. Immuno. 12:635-673 (1994), Yoshimoto, T., et al., Science 270:1845-1847 (1995)]. Multiple signaling pathways were identified for NK1.1 T cells activation. It is assumed that $NK1.1^+$ T cells are not stably polarized, and upon different triggers TCR engagement triggers both Th1 and Th2 cytokine secretion from these cells [Bendelac, A., et al., Annu. Rev. Immunol. 15:535-562 (1997); Arase, H., et al., J. Immunol. 151:546 (1993); Kawamura, T., et al., J. Immunol. 160:16-19 (1998), Chen, H., et al., J. Immonol., 159:2240-2249 (1997); Arase, H, et al., Eur. J. Immunol. 23: 307-310 (1998); Yoshimoto, T., J. Exp. Med. 179: 1285-1295 (1994); MacDonald, H. R., J. ibid., (1995)]. NK1.1R or IL12R engagement may selectively promote the Th1 secretion paradigm [Bendelac, et al. (1997) ibid.; Arase, H., et al., J. Exp. Med. 183:2391-2396 (1996); Hayakawa, T., et al., J. Exp. Med. 176:269-274 (1992)].

Therefore, in one specific embodiment, the invention provides for a method for immuno-modulation resulted by shifting of the Th1/Th2 cell balance toward the pro-inflammatory cytokine producing cells, in a subject in need thereof. Accordingly, this method comprises the step of increasing the levels, the expression and/or the activity of leptin in said subject.

More particularly, increasing the levels or the expression of leptin in a subject in need thereof may be performed by administering to said subject an immuno-modulatory effective amount of a protein or nucleic acid that will increase the amount of leptin, the expression of leptin or leptin activity in the subject. Examples of proteins can comprise but not be limited to leptin, homologues of leptin, functional derivatives of leptin, leptin fragments and anti-idiotypic antibodies to leptins. Nucleic acids useful for the purpose of increasing the amount, expression or activity of leptin can be designed to express any of the foregoing proteins. Small molecules such as nicotinic acids, nicotinic acid ester or diphenylethylene compounds that contain either thiazolidinedione or oxazolidinedione moieties may also find use in the present invention. These compounds or reagents may be used alone or they maybe used in combination with each other.

Homologues of leptin refer to proteins, in which one or more of the amino acid residues of a natural leptin are replaced by different amino acid residues, or are deleted, or one or more amino acid residues are added to the natural sequence of leptin, without changing considerably the activity of the resulting products as compared with the wild type leptin. These homologues are prepared by known synthesis and/or by site-directed mutagenesis techniques, or any other known technique suitable therefore.

Any such homologue preferably has a sequence of amino acids sufficiently duplicative of that of leptin, such as to have substantially similar activity to leptin. One such activity may be the ability of a leptin homologue to reduce the body weight of ob/ob mice. Thus, it can be determined whether any given homologue has substantially the same activity as leptin by means of routine experimentation. In a specifically preferred embodiment, leptin homologue is capable of modulating Th1/Th2 cell balance.

In a preferred embodiment, any such protein has at least 40% sequence identity or homology with the sequence of either leptin. More preferably, it has at least 50%, at least 60%, at least 70%, at least 80% or, most preferably, at least 90% sequence identity or homology thereto.

Homologues of leptin polypeptides, which can be used in accordance with the present invention, or nucleic acid coding therefore, include a finite set of substantially corresponding sequences as substitution peptides or polynucleotides which can be routinely obtained by one of ordinary skill in the art, without undue experimentation, based on the teachings and guidance presented herein. For a detailed description of protein chemistry and structure, see Schulz, G. E. et al., Principles of Protein Structure, Springer-Verlag, New York, 1978; and Creighton, T. E., Proteins: Structure and Molecular Properties, W.H. Freeman & Co., San Francisco. 1983, which are hereby incorporated by reference.

Preferred changes for homologues in accordance with the present invention are what are known as "conservative" substitutions. Conservative amino acid substitutions of leptin polypeptides may include synonymous amino acids within a group which have sufficiently similar physicochemical properties that substitution between members of the group will preserve the biological function of the molecule [Grantham, et al., Science 185:862-864 (1974)]. It is clear that insertions and deletions of amino acids may also be made in the sequences of leptin without altering its function, particularly if the insertions or deletions only involve a few amino acids, e.g., under thirty, and preferably under ten, and do not remove or displace amino acids which are critical to a functional conformation, e.g., cysteine residues [Anfinsen, et al., Science 181:223.230 (1973)]. Proteins produced by such deletions and/or insertions come within the purview of the present invention.

It should be noted that any homologue of leptin has an amino acid sequence essentially corresponding to that of leptin. The term "essentially corresponding to" is intended to comprehend proteins with minor changes to the sequence of the natural protein which do not affect the basic characteristics of the natural proteins, particularly insofar as their ability to modulate the immune-system, preferably, towards the pro-inflammatory response. The type of changes which are generally considered to fall within the "essentially corresponding to" language are those which would result from conventional mutagenesis techniques of the DNA encoding these proteins, resulting in a few minor modifications.

"Functional derivatives" as used herein cover derivatives of leptin or its active fragments or fractions and its fusion proteins, which may be prepared from the functional groups which occur as side chains on the residues or the N- or C-terminal groups, by means known in the art, and are included in the invention as long as they remain pharmaceutically acceptable, i.e. they do not destroy the activity of the protein which is substantially similar to the activity of leptin, and do not confer toxic properties on compositions containing it. These derivatives may, for example, include polyethylene glycol side-chains which may mask antigenic sites and extend the residence of leptin or its active fractions in body fluids. Other derivatives include aliphatic esters of the carboxyl groups, amides of the carboxyl groups by reaction with ammonia or with primary or secondary amines, N-acyl derivatives of free amino groups of the amino acid residues formed with acyl moieties (e.g. alkanoyl or carbocyclic aroyl groups) or O-acyl derivatives of free hydroxyl groups (for example that of seryl or threonyl residues) formed with acyl moieties.

As "functional fragments" of leptin and leptin fusion proteins, the present invention covers any fragment or precursors of the polypeptide chain of leptin, or fused proteins containing any such fragment of leptin, alone or together with associated molecules or residues linked thereto, e.g., sugar or phosphate residues, or aggregates of any of the above derivatives, provided said fraction has substantially similar activity to leptin.

Thus, by "functional fragments" is meant "fragments", "variants", "analogs" or "derivatives" of the molecule. A "fragment" of a molecule, such as any of the amino acid sequence of leptin used by the present invention is meant to refer to any amino acid subset of the molecule. A "variant" of such molecule is meant to refer to a naturally occurring molecule substantially similar to either the entire molecule or a fragment thereof. An "analog" of a molecule is a homologous molecule from the same species or from different species. By "functional" is meant having same biological function, for example, required for immuno-modulation.

As indicated above, the terms derivatives and functional derivatives as used herein mean peptides comprising the amino acid sequence of leptin, with any insertions, deletions, substitutions and modifications to the peptide that do not interfere with the peptides ability to modulate Th1/Th2 response (hereafter referred to as "derivative/s"). A derivative should maintain a minimal homology to said amino acid sequence, e.g. not less than 30%. It should be appreciated that the term "insertions" as used herein is meant any addition of amino acid residues to the peptides used by the invention, between 1 to 50 amino acid residues, preferably, between 20 to 1. amino acid residues and most preferably, between 1 to 10 amino acid residues.

As indicated by said preferred embodiment, enhancing the levels of leptin in a subject in need thereof may be accomplished by the use of expression vectors encoding leptin or leptin homologues, provided by gene therapy.

As used herein, the term "nucleic acid" refers to polynucleotides such as deoxyribonucleic acid (DNA), and, where appropriate, ribonucleic acid (RNA). The terms should also be understood to include, as equivalents, analogs of either RNA or DNA made from nucleotide analogs, and, as applicable to the embodiment being described, single-stranded and double-stranded polynucleotides. "Construct" or "vectors", as used herein, encompases vectors such as plasmids, viruses, bacteriophage, integratable DNA fragments, and other vehicles, which enable the integration of DNA fragments into the genome of the host. Expression vectors are typically self-replicating DNA or RNA constructs containing the desired gene or its fragments, and operably linked genetic control elements that are recognized in a suitable host cell and effect expression of the desired genes. These control elements are capable of effecting expression within a suitable host. Generally, the genetic control elements can include a prokaryotic promoter system or a eukaryotic promoter expression control system. This typically include a transcriptional promoter, an optional operator to control the onset of transcription, transcription enhancers to elevate the level of RNA expression, a sequence that encodes a suitable ribosome binding site, RNA splice junctions, sequences that terminate transcription and translation and so forth. Expression vectors usually contain an origin of replication that allows the vector to replicate independently of the host cell.

A vector may additionally include appropriate restriction sites, antibiotic resistance or other markers for selection of vector-containing cells. Plasmids are the most commonly used form of vector but other forms of vectors which serves an equivalent function and which are, or become, known in the art are suitable for use herein. See, e.g., Pouwels et al., Cloning Vectors: a Laboratory Manual (1985 and supplements), Elsevier, N.Y.; and Rodriguez, et al. (eds.) Vectors: a Survey of Molecular Cloning Vectors and their Uses, Buttersworth, Boston, Mass. (1988), which are incorporated herein by reference.

It should be further appreciated that the invention further encompasses the use of a host cell transformed or transfected with a construct expressing leptin or any fragments thereof. Suitable host cells include prokaryotes, lower eukaryotes, and higher eukaryotes. Prokaryotes include gram negative and gram positive organisms, e.g., *E. coli* and *B. subtilis*. Lower eukaryotes include yeast, *S. cerevisiae* and *Pichia*, and species of the genus *Dictyostelium*. Higher eukaryotes include established tissue culture cell lines from animal cells, both of non-mammalian origin, e.g., insect cells and birds, and of mammalian origin, e.g., human and other primate, and of rodent origin.

"Host cell" as used herein refers to cells which can be recombinantly transformed with vectors constructed using recombinant DNA techniques. A drug resistance or other selectable marker is intended in part to facilitate the selection of the transformants. Additionally, the presence of a selectable marker, such as drug resistance marker may be of use in keeping contaminating microorganisms from multiplying in the culture medium. Such a pure culture of the transformed host cell would be obtained by culturing the cells under conditions which require the induced phenotype for survival.

As used herein, the term "transfection" means the introduction of a nucleic acid, e.g., an expression vector, into a recipient cells by nucleic acid-mediated gene transfer. "Transformation", as used herein, refers to a process in which a cell's genotype is changed as a result of the cellular uptake of exogenous DNA or RNA.

"Cells", "host cells" or "recombinant cells" are terms used interchangeably herein. It is understood that such terms refer not only to the particular subject cells but to the progeny or potential progeny of such a cell. Because certain modification may occur in succeeding generation due to either mutation or environmental influences, such progeny may not, in fact, be identical to the parent cell, but are still included within the scope of the term as used herein.

According to a specifically preferred embodiment, the method of the invention is particularly useful for shifting of the Th1/Th2 cell balance toward the proinflammatory cytokine producing cells a mammalian subject suffering of an immune-related disorder.

More preferably, shifting of the Th1/Th2 cell balance toward the proinflammatory cytokine producing cells may be particularly advantageous for immune-related disorder such as malignant proliferative disorder a disorder caused by immuno-suppression and an infection caused by a pathogenic agent.

According to one embodiment, a malignant proliferative disorder may be any one of solid and non-solid tumor selected from the group consisting of carcinoma, sarcoma, melanoma, leukemia and lymphoma. In cancerous situations, modulation of the NK T cells by leptin, as showed by the Examples may be in the direction of inducing a pro-inflammatory response. As used herein to describe the present invention, "cancer", "tumor" and "malignancy" all relate equivalently to a hyperplasia of a tissue or organ. If the tissue is a part of the lymphatic or immune systems, malignant cells may include non-solid tumors of circulating cells. Malignancies of other tissues or organs may produce solid tumors. In general, the methods and compositions of the present invention may be used in the treatment of non-solid and solid tumors, for example, carcinoma, sarcoma, melanoma, leukemia, and lymphoma.

Malignancies that may find utility in the present invention can comprise but are not limited to hematological malignancies (including leukemia, lymphoma and myeloproliferative disorders), hypoplastic and aplastic anemia (both virally induced and idiopathic), myelodysplastic syndromes, all types of paraneoplastic syndromes (both immune mediated and idiopathic) and solid tumors.

More specifically, according to a preferred embodiment, modulation of leptin or leptin activity, could be used for the treatment or inhibition of non-solid cancers, e.g. hematopoietic malignancies such as all types of leukemia, e.g. acute lymphocytic leukemia (ALL), acute myelogenous leukemia (AML), chronic lymphocytic leukemia (CLL), chronic myelogenous leukemia (CML), myelodysplastic syndrome (MDS), mast cell leukemia, hairy cell leukemia, Hodgkin's disease, non-Hodgkin's lymphomas, Burkitt's lymphoma and multiple myeloma, as well as for the treatment or inhibition of solid tumors such as tumors in lip and oral cavity, pharynx, larynx, paranasal sinuses, major salivary glands, thyroid gland, esophagus, stomach, small intestine, colon, colorectum, anal canal, liver, gallbladder, extraliepatic bile ducts, ampulla of vater, exocrine pancreas, lung, pleural mesothelioma, bone, soft tissue sarcoma, carcinoma and malignant melanoma of the skin, breast, vulva, vagina, cervix uteri, corpus uteri, ovary, fallopian tube, gestational trophoblastic tumors, penis, prostate, testis, kidney, renal pelvis, ureter, urinary bladder, urethra, carcinoma of the eyelid, carcinoma of the conjunctiva, malignant melanoma of the conjunctiva, malignant melanoma of the uvea, retinoblastoma, carcinoma of the lacrimal gland, sarcoma of the orbit, brain, spinal cord, vascular system, hemangiosarcoma and Kaposi's sarcoma.

According to another particular embodiment, as also shown by the Examples, the method of the invention may be advantageous for Hepatocellular carcinoma (HCC). Hepatocellular carcinoma (HCC) is the seventh leading cause of cancer-related mortality in men and the ninth in women. [Bosch, F. X. and Munoz, N. In: Etiology, patology and treatment of hepatocellular carcinoma in America. Advaces in applied technology series. Tabor E, Dibiscegile A M, Purcell Rh (Eds.), Gulf, Houston (1991)]. The prevalence of the disease is steadily increasing in the western world, mainly due to a growing pool of longstanding chronic HCV carriers. An estimated one million deaths are caused annually from HCC [El Serag, H. B. et al., Ann. Intern. Med. 18:139(10): 817-23 (2003)]. HCC is resistant to systemic chemotherapy and radiation treatment. Chemoembolisation, ethanol injection, radiofrequency ablasion, and tumor resection offer a slight prognostic advantage and are mainly used as palliative measures. Orthotopic liver transplantation may offer cure in small tumors, but is rarely employed [Llovet, J. M. et al., Lancet. 6:362(9399): 1907-17 (2003)]. Therefore, modulation of the immune response towards a pro-inflammatory response by the use of leptin, is advantageous.

In another preferred embodiment, the subject in need of modulating the Th1/Th2 cell balance toward the pro-inflammatory cytokine producing cells by the method of the invention may suffer from any immuno-suppressive disorder, for example immune suppression caused by infection of immunodeficiency virus, preferably, HIV, or alternatively, immunosuppression caused by chemotherapy. Chemotherapeutic treatment in malignancy is often associated with life-threatening opportunistic infections, resulting from potent inhibition of various arms of the immune system. Often, the intensity and duration of chemotherapeutic treatment are limited by these side effects. Stimulation of the immune system, optionally by the coadministration of leptin may enable treatment with higher doses and more potent combinations of chemotherapeutic agents, thereby reducing the risks of medication-induced immune suppression.

According to another embodiment, shifting of the Th1/Th2 cell balance toward the pro-inflammatory cytokine producing cells by the method of the invention may be advantageous in a subject suffering of an infection, for example infection caused by a pathogenic agent.

Reference to pathogenic agents includes a prokaryotic microorganism, a lower eukaryotic microorganism, a complex eukaryotic organism, a virus, fungi, prions, parasite, yeast and venoms.

A prokaryotic microorganism includes bacteria such as Gram positive, Gram negative and Gram variable bacteria and intracellular bacteria. Examples of bacteria contemplated herein include the speices of the genera *Treponema* sp., *.Borrelia* sp., *Neisseria* .sp., *Legionella* sp., *Bordetella* sp., *Escherichia* sp., *Salmonella* sp., *Shigella* sp., *Klebsiella* sp., *Yersinia* sp., *Vibrio* sp., *Hemophilus* sp., *Rickettsia* sp., *Chlamydia* sp., *Mycoplasma* sp., *Staphylococcus* sp., *Streptococcus* sp., *Bacillus* sp., *Clostridium* sp., *Corynebacterium* sp., *Proprionibacterium* sp., *Mycobacterium* sp., *Ureaplasma* sp. and *Listeria* sp.

Particularly preferred species include *Treponema pallidum, Borrelia burgdorferi, Neisseria gonorrhea, Neisseria meningitidis, Legionella pneumophila, Bordetella pertussis, Escherichia coli, Salmonella typhi, Salmonella typhimurium, Shigella dysenteriae, Klebsiella pneumoniae, Yersinia pestis, Vibrio cholera, Hemophilus influenzae, Rickettsia rickettsii, Chlamydia trachomatis, Mycoplasma pneumoniae, Staphylococcus aureus, Streptococcus pneumoniae, Streptococcus pyogenes, Bacillus anthracis, Clostridium botulinum, Clostridium tetani, Clostridium perfringens, Corynebacterium diphtheriae, Proprionibacterium acnes, Mycobacterium tuberculosis, Mycobacterium leprae* and *Listeria monocytogenes.*

A lower eukaryotic organism includes a yeast or fungus such as but not limited to *Pneumocystis carinii, Candida albicans, Aspergillus, Histoplasma capsulatum, Blastomyces dermatitidis, Cryptococcus neoformans, Trichophyton* and *Microsporum.*

A complex eukaryotic organism includes worms, insects, arachnids, nematodes, aemobe, *Entamoeba histolytica, Giardia lam blia, Trichomonas vaginalis, Trypanosoma brucei gambiens, Trypanosoma cruzi, Balantidium coli, Toxoplasma gondii, Cryptosporidium* or *Leishmania.*

The term "viruses" is used in its broadest sense to include viruses of the families adenoviruses, papovaviruses, herpesviruses: simplex, varicella-zoster, Epstein-Barr, CMV, pox viruses: smallpox, vaccinia, hepatitis B, rhinoviruses, hepatitis A, poliovirus, rubellavirus, hepatitis C, arboviruses, rabiesvirus, influenzaviruses A and B, measlesvirus, mumpsvirus, HIV, HTLV I and II.

The term "fungi" includes for example, fungi that cause diseases such as ringworm, histoplasmosis, blastomycosis, aspergillosis, cryptococcosis, sporotrichosis, coccidioidomycosis, paracoccidio-idoinycosis, and candidiasis.

The term parasite includes, but not limited to, infections caused by somatic tapeworms, blood flukes, tissue roundworms, ameba, and *Plasmodium, Trypanosoma, Leishniania,* and *Toxoplasma* species.

The invention further provides for a method for the treatment of an immune-related disorder in a subject in need thereof, comprising the step of administering to said subject an immuno-modulatory effective amount of a protein or nucleic acid that will increase the amount of leptin, the expression of leptin or leptin activity in the subject. Examples of proteins can comprise but not be limited to leptin, homologues of leptin, functional derivatives of leptin, leptin fragments and anti-idiotypic antibodies to leptins. Nucleic acids useful for the purpose of increasing the amount, expression or activity of leptin can be designed to express any of the foregoing proteins. Small molecules such as nicotinic acids, nicotinic acid ester or diphenylethylene compounds that contain either thiazolidinedione or oxazolidinedione moieties may also find use in the present invention. These compounds or reagents may be used alone or they maybe used in combination with each other.

As used herein in the specification and in the claims section below, the term "treat" or treating and their derivatives includes substantially inhibiting, slowing or reversing the progression of a condition, substantially ameliorating clinical symptoms of a condition or substantially preventing the appearance of clinical symptoms of a condition.

As used herein, "an immuno-modulatory amount" or "an amount sufficient to modulate the Th1/Th2 balance" means an amount necessary to achieve a selected therapeutic result. For example, in this particular embodiment an effective amount of the composition of the invention will modulate the Th1/Th2 balance toward pro-inflammatory cytokine producing cells.

Thus, in one embodiment, the effective amount administered to a subject suffering from an immune-related disorder may be an amount sufficient for shifting the Th1/Th2 cell balance toward pro-inflammatory cytokine producing cells.

According to another embodiment, the method of the invention is particularly applicable for the treatment of an immune-related disorder such as a malignant proliferative disorder, a disorder caused by immuno-suppression or an infection caused by a pathogenic agent as described above.

More particularly, the method of the invention is particularly applicable for the treatment of a malignant proliferative disorder such as solid and non-solid tumors selected from the group consisting of carcinoma, sarcoma, melanoma, leukemia and lymphoma.

According to a specifically preferred embodiment, the method of the invention is for the treatment of Hepatocellular carcinoma (HCC).

According to another embodiment, the method of the invention is suitable for the treatment of immuno-suppression caused by infection of an immunodeficiency virus, preferably, HIV, or caused by chemotherapy.

Still further, the method of the invention is intended for the treatment of an infection caused by a pathogenic agent, for example, bacterial pathogens, viruses, fungi, parasites or yeast.

In another aspect, the invention relates to the use of a protein or nucleic acid that will increase the amount, expression or activity of leptin for the preparation of a composition for shifting the Th1/Th2 cell balance toward pro-inflammatory cytokine producing cells.

The invention further relates to the use a protein or nucleic acid that will increase the amoun, expression or activity of leptin for the preparation of a medicament for the treatment of an immune-related disorder.

According to one embodiment of said aspect, the immune-related disorder may be a malignant proliferative disorder, a disorder caused by immuno-suppression or an infection caused by a pathogenic agent.

Specifically, a malignant proliferative disorder may be solid and non-solid tumors selected from the group consisting of carcinoma, preferably, Hepatocellular carcinoma (HCC), sarcoma, melanoma, leukemia and lymphoma.

In another embodiment, the immune related disorder may be immuno-suppression, for example, caused by infection of immunodeficiency virus, preferably, HIV, or alternatively, by chemotherapy.

In yet another embodiment, the immune related disorder may be infection caused by a pathogenic agent selected from the group consisting of bacterial pathogens, viruses, fungi, parasites and yeast.

The role of leptin in modulation of the Th1/Th2 response and in the induction of a pro-inflammatory response, enables the manipulation of this element such that, for example, its neutralization will favor induction of an anti-inflammatory response.

Therefore, in a third aspect, the invention relates to a method for immuno-modulation of the immune system resulted by shifting the Th1/Th2 cell balance toward the anti-inflammatory cytokine producing cells, in a subject in need thereof. Such method comprises the step of decreasing the amounts, the expression and/or the activity of leptin in said subject.

According to one embodiment, decreasing the amounts, the expression or the activity of leptin in said subject by the method of the invention may be performed by administering to a subject in need thereof, an immuno-modulatory effective amount of proteins or nucleic acids where the proteins can comprise but not be limited to leptin fragments, antibodies to leptin, fragments of antibodies to leptin, soluble leptin receptor, fragments of the leptin receptor, antibodies to the leptin receptor and fragments of antibodies to leptin receptor, gala- nin and the SOCS-3 gene product and the nucleic acids can comprise but not be limited to oligonucleotides or nucleic acids that act as antisense, ribozymes or siRNA or that code for expression of antisense RNA, ribozymes or siRNA. These compounds or reagents may be used alone or they maybe used in combination with each other.

The term "antibody" is meant to encompass polyclonal antibodies, monoclonal antibodies (mAbs), chimeric antibodies (e.g., humanized antibodies) and antibody fragments that retain the biological activity of specific binding to leptin, such as Fab, Fab', F(ab')2 and Fv. Also encompassed are single-chain antibodies (sFvs). These antibody fragments lack the Fc portion of an intact antibody, clear more rapidly from the circulation and can have less non-specific tissue binding than an intact antibody. These fragments are produced by well-known methods in the art, for example by proteolytic cleavage with enzymes such as papain (to produce Fab fragments) or pepsin (to produce F(ab')2 fragments).

Polyclonal antibodies are heterogeneous populations of antibody molecules derived from the sera of animals immunized with an antigen. A monoclonal antibody (mAb) contains a substantially homogenous population of antibodies specific to antigens, which population contains substantially similar epitope binding sites. MAbs may be obtained by methods known to those skilled in the art. See, for example Kohler and Milstein, Nature 256:495-497, 1975; U.S. Pat. No. 4,376,110; Ausubel et al, eds., *Current Protocols in Molecular Biology*, Green Publishing Assoc. and Wiley Interscience, N.Y., 1987, 1992; and Harlow and Lane *Antibodies. A Laboratory Manual* Cold Spring Harbor Laboratory, 1988; Colligan et al, eds., *Current Protocols in Immunology*, Greene Publishing Assoc. and Wiley Interscience, N.Y., 1992, 1993; the contents of which references are incorporated entirely herein by reference. Such antibodies can be of any immunoglobulin class including IgG, IgM, IgE, IgA, and any subclass thereof A hybridoma producing a mAb of the present invention can be cultivated in vitro, in situ, or in vivo. Production of high titers of mAbs in vivo or in situ makes this the presently preferred method of production.

Chimeric antibodies which include humanized antibodies, are molecules wherein different portions of which are derived from different animal species, such as those having variable regions derived from a murine mAb and a human immunoglobulin constant region. Chimeric antibodies are primarily used to reduce immunogenicity in application and/or to increase yields in production, for example. Chimeric antibodies and methods for their production are known in the art [Cabilly, et al., Proc. Natl. Acad. Sci. USA 81:3273-3277 (1984); Morrison, et al., Proc. Natl. Acad. Sci. USA 81:6851-6855 (1984); Boulianne, et al., Nature 312:643-646 (1984)]. These references are entirely incorporated herein by reference.

Typically, antibodies that may be used for reducing leptin levels or function by the methods of the present invention are high affinity anti-leptin antibodies, and fragments or regions thereof that have potent inhibiting and/or neutralizing activity in vivo against leptin. Such antibodies can include those generated by immunization using purified recombinant leptin or peptide fragments thereof.

Methods for determining antibody specificity and affinity can be found in Harlow, et al., *Antibodies: A Laboratory Manual*, Cold Spring Harbor Laboratory Press, Cold Spring Harbor, N.Y., 1988; Colligan et al., eds., *Current Protocols in Immunology*, Greene Publishing Assoc. and Wiley Interscience, NY., 1992, 1993; and Muller, *Meth. Enzymol.*, 92:589-601 1983; which references are entirely incorporated herein by reference.

The generation of polyclonal antibodies against proteins is described in Chapter 2 of Current Protocols in Immunology, Wiley and Sons Inc. Monoclonal antibodies may be prepared from B cells taken from the spleen or lymph nodes of immunized animals, in particular rats or mice, by fusion with immortalized B cells under conditions which favor the growth of hybrid cells. For fusion of murine B cells, the cell line Ag-8 is preferred. The technique of generating monoclonal antibodies is described in many articles and textbooks, such as the above-noted Chapter 2 of Current Protocols in Immunology. Spleen or lymph node cells of these animals may be used in the same way as spleen or lymph node cells of protein-immunized animals, for the generation of monoclonal antibodies as described in Chapter 2 therein. The techniques used in generating monoclonal antibodies are further described by Kohler and Milstein, Nature 256:495-497, (1975), and in U.S. Pat. No. 4,376,110.

As indicated above, for future clinical applications, where the antibody is a monoclonal antibody, it may be improved, through a humanization process, to overcome the human antibody to mouse antibody response. Rapid new strategies have been developed recently for antibody humanization which may be applied for such an antibody. These technologies maintain the affinity, while retaining antigen and epitope specificity of the original antibody Rader, C., et al., Proc. Natl. Acad. Sci. 95:8910-8915 (1998); Mateo, C., et al., Immunotechnology 3:71-81 (1997)]. A "humanized" antibody, in which, for example animal (say murine) variable regions are fused to human constant regions, or in which murine complementarity-determining regions are grafted onto a human antibody. Unlike, for example, animal derived antibodies, "humanized" antibodies often do not undergo an undesirable reaction with the immune system of the subject.

Thus, as used herein, the term "humanized" and its derivatives refers to an antibody which includes any percent above zero and up to 100% of human antibody material, in an amount and composition sufficient to render such an antibody less likely to be immunogenic when administered to a human being. It is understood that the term "humanized" reads also on human derived antibodies or on antibodies derived from non human cells genetically engineered to include functional parts of the human immune system coding genes, which therefore produce antibodies which are fully human.

Reducing the amount, expression and activity of leptin by the method of the invention may be also achieved by the use of particular nucleic acid sequences, such as anti-sense sequence, siRNA and a catalytic nucleic acid sequence such as ribozyme that are specific for leptin or the leptin receptor. The term "siRNAs" refers to short interfering RNAs. The term "RNA interference" or "RNAi" refers to the silencing or decreasing of gene expression by siRNAs. It is the process of sequence-specific, post-transcriptional gene silencing in animals and plants, initiated by siRNA that is homologous in its duplex region to the sequence of the silenced gene. The gene may be endogenous or exogenous to the organism, present integrated into a chromosome or present in a transfection vector that is not integrated into the genome. The expression of the gene is either completely or partially inhibited. RNAi may also be considered to inhibit the function of a target RNA; the function of the target RNA may be complete or partial. RNA interference (RNAi) is a mechanism involving double-stranded RNA (dsRNA) molecules and resulting in posttranscriptional sequence-specific silencing of gene expression.

As indicated above, ribozymes may also be used. Ribozymes are RNA molecules having an enzymatic activity which is able to repeatedly cleave other separate RNA molecules in a nucleotide base sequence specific manner. Several basic varieties of naturally-occurring enzymatic RNAs are known presently. Each can catalyze the hydrolysis of RNA phosphodiester bonds in-trans (and thus can cleave other RNA molecules) under physiological conditions. In general, enzymatic nucleic acids act by first binding to a target RNA. Such binding occurs through the target binding region of a enzymatic nucleic acid which is held in close proximity to an enzymatic region or catalytic region of the molecule that acts to cleave the target RNA. Thus, the enzymatic nucleic acid first recognizes and then binds a target RNA through complementary base-pairing, and once bound to the correct site, acts enzymatically to cut the target RNA. Strategic cleavage of such a target RNA will destroy its ability to direct synthesis of an encoded protein, and according to the present invention, the expression of leptin. After an enzymatic nucleic acid has bound and cleaved its RNA target, it is released from that RNA to search for another target and can repeatedly bind and cleave new targets. Thus, a single ribozyme molecule is able to cleave many molecules of target RNA. In addition, the ribozyme is a highly specific inhibitor of gene expression, with the specificity of inhibition depending not only on the base-pairing mechanism of binding to the target RNA, but also on the mechanism of target RNA cleavage. Single mismatches, or base-substitutions, near the site of cleavage can completely eliminate catalytic activity of a ribozyme.

According to a specific embodiment, a subject may be a mammalian subject suffering of an immune-related disorder.

More particularly, the immune-related disorder may be any one of an inflammatory disorder, an autoimmune-disorder, a graft-rejection associated disorder or a fibrotic disorder.

Therefore, in a further embodiment, proteins and nucleic acids that decrease the amount, expression or activity of leptin may be used for treatment of or amelioration of inflammatory symptoms in any disease, condition or disorder where immune and/or inflammation suppression is beneficial such as, but not limited to, treatment of or amelioration of inflammatory symptoms in the joints, musculoskeletal and connective tissue disorders, or of inflammatory symptoms associated with hypersensitivity, allergic reactions, asthma, atherosclerosis, otitis and other otorhinolaryngological diseases, dermatitis and other skin diseases, posterior and anterior uveitis, conjunctivitis, optic neuritis, scleritis and other immune and/or inflammatory ophthalmic diseases.

Diseases characterized by airway inflammation affect a substantial proportion of the population. These diseases include asthma and chronic obstructive pulmonary disease (COPD). In the European Union, COPD and asthma, together with pneumonia, are the third most common cause of death. The production of cytokines and growth factors in response to irritants, infectious agents and inflammatory mediators play an important role in the initiation, perpetuation and inhibition of acute and chronic airway inflammation.

Airway inflammation is associated with excessive production and activity of several mediators and cytokines released by inflammatory and resident cells in the airways. Now it is clear that the epithelium is not only an important target for the action of mediators of inflammation, but also an active participant in the inflammatory process itself. Bronchial epithelial cells are able to recruit inflammatory cells to the airways through the release of chemoattractants, to direct inflammatory cell migration across the epithelium through the expression of cell adhesion molecules, and to regulate the inflammatory activity of other cells through the release of mediators, like cytokines, chemokines, arachidonic acid metabolities and relaxant and contractile factors.

In one embodiment, an inflammatory disorder may be an intestinal inflammatory disease, preferably, an inflammatory bowel diseases (IBD).

Inflammatory bowel diseases (IBD) are common gastrointestinal disorders, that can be perceived as being the result of a dysbalance between Th1-pro-inflammatory, and Th2-anti-inflammatory subtypes of immune responses [Strober, W., et al., Immunol Today 18:61-64 (1997); Neurath, M., et al., J. Exp. Med. 183:2605-2616 (1996)].

There are several extra-intestinal manifestations that accompany IBD, for example: autoimmune phenomena since immune complexes have a role in target organ damage, immunosuppressive agents such as glucocorticoids, azathioprine, methotrexate and cyclosporin are used to alleviate the disease [Podolsky, D. K., et al., New Engl. J. Med., 325:928-935(1991); Strober, W., et al., In Clinical Immunology, Mosby, St. Louis. R. R. Rich, Editor, 1401-14281-2 (1995)]. Patients with IBD have antibodies against components of colon cells and several different bacterial antigens. These antigens gain access to the immune system as a consequence of epithelial damage [Hibi, S., et al., Clin. Exp. Immunol. 54:163-168 (1983); Das, K. M., et al., Gastroenterology 98:464-69 (1990)]. Abnormalities of T cell-mediated immunity, including coetaneous anergy and diminished responsiveness to T cell stimuli, have also been described in these patients [Chiba, M., et al., Gut, 22:177-182 (1981); Raedler, A., et al., Clin. Exp. Immunol. 60:518-526 (1985)]. In addition, changes in mucosal cell mediated immunity were identified, including increased concentrations of mucosal IgG cells and changes in T cells subsets, suggesting antigen stimulation [Dasgupta, A., et al., Gut 35:1712-17 (1994); Takahashi, F., et al., J. Clin. Invest. 76:311-318 (1985)]. Exposure of target antigens after infectious, immune, or toxic damage, leads to activation of mucosal immune cells resulting in cytokines that lead to mucosal inflammatory response [Neurath, M., et al., J. Exp. Med., 183:2605-2616 (1996)]. Secretion of pro-inflammatory cytokines such as IFNγ, contributes to an increase in mucosal permeability, and has been described in animal models of IBD [Strober, W., et al., Immunol. Today 18:61-64. (1997)]. Similarly, an increase in collagen synthesis mediated by IL1 and IL6 can be detected in these animals [Strober, W., et al., ibid.]. A Th1-mediated granulomatous colitis model has been established by the adoptive transfer of normal CD45RB T cells from Balb/C mice into CB-17 scid mice. CD4 cells from CD45RB were shown to prevent the disease when injected together with the CD45RB population. This prevention could be reversed by adding antibodies to TGFJB1 [Sadlack, B., et al., Cell 75:253-261 (1993); Powrie, F., et al., Immunity 1:553-562 (1994)].

Furthermore, the present invention discloses the use of leptin fragments, antibodies to leptin, fragments of antibodies to leptin, soluble leptin receptor, fragments of the leptin receptor, antibodies to the leptin receptor and fragments of antibodies to leptin receptor, galanin and the SOCS-3 gene product as well as oligonucleotides or nucleic acids that act as antisense, ribozymes or siRNA or that code for expression of antisense RNA, ribozymes or siRNA or any combination of the foregoing when an immune-mediated disorder comprises an allergy, asthma or a parasitic infection. The present invention may find further use when said immune-mediated disorder comprises an over-reactive immune response directed against infectious agents such as a virus or a bacterium. Often in these diseases, production of autoreactive antibodies and/or autoreactive T lymphocytes can be a result of this over-response. For example, when IgE is overproduced or when a disease is Th2 dependent, the reaction itself can be detrimental to the organism as, for example, seen with some parasitical diseases or with mycobacterial infections such as TBC or leprosy. An autoimmune response may also occur as a manifestation of a viral or bacterial infection and may result in severe tissue damage, as for example, lymphocytic choriomeningitis virus (LCMV) infections or the destructive hepatitis caused by Hepatitis B infection.

In another preferred embodiment, decreasing the levels or activity of leptin by the methods of the invention are useful for treatment of or amelioration of an autoimmune disease such as, but not limited to, Eaton-Lambert syndrome, Goodpasture's syndrome, Greave's disease, Guillain-Barr syndrome, autoimmune hemolytic anemia (AIHA), hepatitis, insulin-dependent diabetes mellitus (IDDM), systemic lupus erythematosus (SLE), multiple sclerosis (MS), myasthenia gravis, plexus disorders e.g. acute brachial neuritis, polyglandular deficiency syndrome, primary biliary cirrhosis, rheumatoid arthritis, scleroderma, thrombocytopenia, thyroiditis e.g. Hashimoto's disease, Sjbgren's syndrome, allergic purpura, psoriasis, mixed connective tissue disease, polymyositis, dermatomyositis, vasculitis, polyarteritis nodosa, polymyalgia rheumatica, Wegener's granulomatosis, Reiter's syndrome, Behget's syndrome, ankylosing spondylitis, pemphigus, bullous pemphigoid, dennatitis herpetiformis, insulin dependent diabetes, inflammatory bowel disease, ulcerative colitis and Crohn's disease.

The present invention further provides for a method for the treatment of an immune-related disorder in a subject in need thereof. The method of the invention comprises the step of administering to said subject an immuno-modulatory effective amount of proteins or nucleic acids where the proteins can comprise but not be limited to leptin fragments, antibodies to leptin, fragments of antibodies to leptin, soluble leptin receptor, fragments of the leptin receptor, antibodies to the leptin receptor and fragments of antibodies to leptin receptor, galanin and the SOCS-3 gene product and the nucleic acids can comprise but not be limited to oligonucleotides or nucleic acids that act as antisense, ribozymes or siRNA or that code for expression of antisense RNA, ribozymes or siRNA. These compounds or reagents may be used alone or they may be used in combination with each other.

It should be noted that composition dosages administered by the methods of the invention may be in any amount that sufficient to modulate the Th1/Th2 balance. It is understood by the skilled artisan that the preferred dosage would be individualized to the patient following good laboratory practices and standard medical practices. As used herein, "an amount sufficient to modulate the Th1/Th2 balance" means an amount necessary to achieve a selected result. For example, in the foregoing embodiment an effective amount of the composition of the invention will modulate the Th1/Th2 balance toward anti-inflammatory cytokine producing cells.

Thus, according to one embodiment, an effective amount may be an amount sufficient for shifting the Th1/Th2 cell balance toward anti-inflammatory cytokine producing cells.

In another embodiment, the method of the invention is intended for the treatment of an immune-related disorder such as inflammatory disorder, an autoimmune-disorder a graft-rejection associated disorder or a fibrotic disorder.

According to a specific embodiment, the method of the invention is particularly advantageous for the treatment of an inflammatory disorder, preferably, an intestinal inflammatory disease and most preferably, inflammatory bowel diseases (IBD).

According to another specific embodiment, the method of the invention is suitable for the treatment of a fibrotic disorder such as any one of hepatic fibrosis, cardiac fibrosis or colon fibrosis.

Still further, the method of the invention may be applicable for the treatment of auto-immune disease, such as arthritis, diabetes or immune-related infertility disorders.

According to another aspect, the invention relates to the administration proteins or nucleic acids that will decrease the amount of leptin, the expression of leptin or leptin activity for the preparation of a composition that shifts the Th1/Th2 balance towards anti-inflammatory cytokine producing cells. Examples of proteins can comprise but not be limited to leptin fragments, antibodies to leptin, fragments of antibodies to leptin, soluble leptin receptor, fragments of the leptin receptor, antibodies to the leptin receptor and fragments of antibodies to leptin receptor, galanin and the SOCS-3 gene product. Examples of nucleic acids can comprise but not be limited to oligonucleotides or nucleic acids that act as antisense, ribozymes or siRNA or that code for expression of antisense RNA, ribozymes or siRNA. These compounds or reagents may be used alone or they maybe used in combination with each other.

The invention further provides for the use administration of proteins or nucleic acids that will decrease the amount of leptin, the expression of leptin or leptin activity for the preparation of a medicament for the treatment of an immune-relate disorder. Examples of proteins can comprise but not be limited to leptin fragments, antibodies to leptin, fragments of antibodies to leptin, soluble leptin receptor, fragments of the leptin receptor, antibodies to the leptin receptor and fragments of antibodies to leptin receptor, galanin and the SOCS-3 gene product. Examples of nucleic acids can comprise but not be limited to oligonucleotides or nucleic acids that act as antisense, ribozymes or siRNA or that code for expression of antisense RNA, ribozymes or siRNA. These compounds or reagents may be used alone or they maybe used in combination with each other.

According to one embodiment, an immune-related disorder may be an inflammatory disorder, an autoimmune-disorder, a graft-rejection associated disorder or a fibrotic disorder.

More specifically, an inflammatory disorder may be an intestinal inflammatory disease, preferably, inflammatory bowel diseases (IBD).

In another embodiment, the immune related disorder may be a fibrotic disorder such as hepatic fibrosis, cardiac fibrosis or colon fibrosis.

In yet another embodiment, the immune-related disorder may be an auto-immune disease, for example, arthritis, diabetes and immune-related infertility disorders.

In yet a further aspect, the invention relates to a method for the treatment of immune-related disorders in a mammalian subject in need of such treatment, by manipulating NK T cell population of said subject, wherein manipulation of said NK T cell population results in modulation of the Th1/Th2 cell balance, said method comprises the steps of: (a) obtaining NK T cells from said subject; (b) ex vivo educating the NK T cells obtained in step (a) by culturing the NKT cells in the presence of (i) an antigen or antigens associated with said immune-related immune disorder; (ii) an antigen presenting cell, preferably DC and (iii) leptin, a leptin homologue, a modified leptin, a functional leptin fragment, a nucleic acid construct expressing any of the foregoing or any combination thereof such that the resulting educated NK T cells have the capability of modulating the Th1/Th2 cell balance; and (c) re-introducing to said subject the educated NK T cells obtained in step (b) which are capable of modulating the Th1/Th2 cell balance.

The NK T cells educated by the method of the invention can be obtained from bone marrow, liver, spleen, or uterus, but can also be obtained from the peripheral blood, by cytopheresis, a procedure by which a large number of white cells are obtained, while other blood components are being simultaneously transferred back to the subject.

It should be noted that several cell types appear to be capable of serving as APC's (antigen presenting cells), including dendritic cells (DC), activated B cells, and activated macrophages. In accordance with the invention, the APCs used for co-culturing with NK T cells, are preferably autologous cells and in some illustrative preferred embodiments the antigen-presenting cell may be a dendritic cell (DC). It is understood that one of skill in the art will recognize that other antigen presenting cells may be useful in the invention, such as B cells activated by lipopolysaccharide, whole spleen cells, peripheral blood macrophages, fibroblasts or non-fractionated peripheral blood mononuclear cells (PBMC). Therefore, the invention is not limited to the exemplary cell types which are specifically mentioned and exemplified herein.

Co-culturing of the NK T cells in the presence of peripheral lymphocytes from patients suffering from the same immune-related disorder or from a treated subject, is also contemplated in the present invention. In order to obtain lymphocytes from a subject, particularly a human subject, blood may be drawn from the patient by the cytopheresis methods described above.

As indicated above, the NK T cells are co-cultured with APC's in the presence of leptin, and an antigen or antigens associated with the immune related disorder in which the subject suffers from.

It should be appreciated that the antigen or antigens associated with an immune-related disorder can be native or non-native with regards to the subject. They can be natural or synthetic, modified or unmodified, whole or fragments thereof. Fragments can be derived from synthesis as fragments or by digestion or other means of modification to create fragments from larger entities. Such antigen or antigens comprise but are not limited to proteins, glycoproteins, enzymes, antibodies, histocompatibility determinants, ligands, receptors, hormones, cytokines, cell membranes, cell components, viruses, viral components, viral vectors, non-viral vectors, whole cells, tissues or organs. The antigen can consist of single molecules or mixtures of diverse individual molecules. The antigen can present itself within the context of viral surface, cellular surface, membrane, matrix, or complex or conjugated with a receptor, ligand, antibody or any other binding partner. Such antigen or antigens can be introduced to the subject alone or with agent or agents that could further contribute to uptake, stability, reactivity or targeting.

Polymerization and degradation, fractionation and chemical modification are all means that can be used to alter the properties of a particular antigen in terms of potential immune responses. These small segments, fragments or epitopes can either be isolated or synthesized.

As a non-limiting example, such antigen may be a combination of different antigens derived from body extracts, preferably of the subject to be treated or from a subject suffering from the same disorder.

The invention further provides for a therapeutic composition for the treatment of an immune-related disorder in a mammalian subject. The composition of the invention comprises as an effective ingredient ex vivo educated autologous NK T cells capable of modulating the Th1/Th2 cell balance, and optionally further comprising pharmaceutically acceptable carrier, diluent, excipient and/or additive.

According to one embodiment, the educated autologous NK T cell used for the composition of the invention may be obtained by ex vivo culture by culturing the NKT cells in the presence of (i) an antigen or antigens associated with said immune-related immune disorder; (ii) an antigen presenting cell, preferably DC and (iii) leptin, a leptin homologue, a modified leptin, a functional leptin fragment, a nucleic acid construct expressing any of the foregoing or any combination thereof.

Methods for in vitro storage, growth or expansion of cells prior to education or to transfer of the cells to the treated subject, are well known to practitioners of the art. When the educated NK T cells intended for use in a transfer are derived from a donor, these cells may also undergo storage, growth or expansion in vivo or in vitro as described above.

It is to be appreciated that the NK T cells may be educated in vivo as well, via any of the methods described above, they can be modulated prior to or at any point of time following exposure to the APC, leptin and antigens related to said disorder.

Cell therapy may be by injection, e.g., intravenously, or by any of the means described herein above. Neither the time nor the mode of administration is a limitation on the present invention. Cell therapy regimens may be readily adjusted taking into account such factors as the possible cytotoxicity of the educated cells, the stage of the disease and the condition of the patient, among other considerations known to those of skill in the art.

It should be noted that any of the components used by the different methods of the invention, e.g., proteins or nucleic acids that increase the amount, expression or activity of leptin, proteins or nucleic acids that decrease the amount, expression or activity of leptin, host cells containing such proteins or nucleic acids or educated NKT cells, may by administered in a single dose, or alternatively in multiple doses. These components may be administered by a single route of administration or alternatively, by at least two different routes of administration.

The proteins or nucleic acids that increase the amount, expression or activity of leptin, proteins or nucleic acids that decrease the amount, expression or activity of leptin, host cells containing such proteins or nucleic acids or educated NKT cells, may be administered directly to the subject to be treated or, depending on the size of the compound, it may be desirable to conjugate them to a carrier prior to their administration. Therapeutic formulations may be administered in any conventional dosage formulation. Formulations typically comprise at least one active ingredient, as defined above, together with one or more acceptable carriers thereof.

Each carrier should be both pharmaceutically and physiologically acceptable in the sense of being compatible with the other ingredients and not injurious to the patient. Formulations include those suitable for oral, rectal, nasal, or parenteral (including subcutaneous, intramuscular, intravenous and intradermal) administration. The formulations may conveniently be presented in unit dosage form and may be prepared by any methods well known in the art of pharmacy. The nature, availability and sources, and the administration of all such compounds including the effective amounts necessary to produce desirable effects in a subject are well known in the art and need not be further described herein.

More specifically, the said proteins or nucleic acids that increase the amount, expression or activity of leptin, proteins or nucleic acids that decrease the amount, expression or activity of leptin, host cells containing such proteins or nucleic acids or educated NKT cells, may be administered by a route selected from oral, intravenous, parenteral, transdermal, subcutaneous, intravaginal, intranasal, mucosal, sublingual, topical and rectal administration and any combinations thereof.

Although the method of the invention is particularly intended for the treatment of immune-related disorders in humans, other mammals are included. By way of non-limiting examples, mammalian subjects include monkeys, equines, cattle, canines, felines, mice, rats and pigs.

The proteins or nucleic acids that increase the amount, expression or activity of leptin, proteins or nucleic acids that decrease the amount, expression or activity of leptin, host cells containing such proteins or nucleic acids or educated NKT cells, may be administered in a single dose, or alternatively in multiple doses. These components may be administered by a single route of administration or alternatively, by at least two different routes of administration. More specifically, said components may be administered by a route selected from oral, intravenous, parenteral, transdermal, subcutaneous, intravaginal, intranasal, mucosal, sublingual, topical and rectal administration and any combinations thereof.

For treating a mammalian subject suffering of an immune-related disorder, for example, cancer, the leptin, homologues of leptin, functional derivatives of leptin, leptin fragments, anti-idiotypic antibodies to leptins, nucleic acid constructs that express any of the foregoing proteins, host cells containing such constructs or educated NKT cells disclosed in various embodiments of the present invention can be administered in a variety of ways. By way of a non-limiting example, these components, may be delivered intravenously, or into a body cavity adjacent to the location of a solid tumor, such as the intraperitoneal cavity, or injected directly into or adjacent to a solid tumor.

It should be noted that all components and compositions used by the methods of the invention may optionally include sustained-release matrices, such as biodegradable polymers, to form therapeutic compositions. A sustained-release matrix, as used herein, is a matrix made of materials, usually polymers, which are degradable by enzymatic or acid/base hydrolysis or by dissolution. Once inserted into the body, the matrix is acted upon by enzymes and body fluids. The sustained-release matrix desirably is chosen from biocompatible materials such as liposomes, Polylactides (polylactic acid), polyglycolide (polymer of glycolic acid), polylactide co-glycolide (co-polymers of lactic acid and glycolic acid) polyanhydrides, poly(ortho)esters, polypeptides, hyaluronic acid, collagen, chondroitin sulfate, carboxylic acids, fatty acids, phospholipids, polysaccharides, nucleic acids, polyamino acids, amino acids such as phenylalanine, tyrosine, isoleucine, polynucleotides and polyvinylpyrrolidone.

The immuno-modulating pharmaceutical compositions according to the present invention may be a solid, liquid or aerosol and may be administered by any known route of administration. Examples of solid therapeutic compositions include pills, creams, and implantable dosage units. The pills may be administered orally or the therapeutic creams may be administered topically.

The implantable dosage units may be administered locally, for example at a tumor site, or may be implanted for systemic release of the therapeutic composition, for example subcutaneously. Examples of liquid compositions include compositions adapted for injection subcutaneously, intravenously, intraarterially, and compositions for topical and intraocular administration. Examples of aerosol compositions include inhaler composition for administration to the lungs.

The leptin, homologues of leptin, functional derivatives of leptin, leptin fragments, anti-idiotypic antibodies to leptins, nucleic acid constructs that express any of the foregoing proteins, host cells containing such constructs or educated NKT cells disclosed in various embodiments of the present invention can be administered by standard routes. In general, the combinations may be administered by the topical (including buccal and sublingual), or parenteral (including subcutaneous, intraperitoneal, intramuscular, intravenous, intradermal, intracerebral, intracerebroventricular, intracranial, intraspinal, intratracheal, and epidural), transdermal, intravaginal, intrauterine, oral, rectal, ophthalmic (including intravitreal or intracameral), or intranasal administration. Osmotic mini-pumps may also be used to provide controlled delivery of high concentrations of leptin, or leptin derivatives, to the site of interest, such as directly into a metastatic growth.

The magnitude of therapeutic dose of the various compositions used in the present invention will of course vary with the group of patients (age, sex, etc.), the nature of the condition to be treated and with the route administration and as such, dosage will be determined by the attending physician.

The pharmaceutical forms suitable for injection use include sterile aqueous solutions or dispersions and sterile powders for the extemporaneous preparation of sterile injectable solutions or dispersions. In all cases the form must be sterile and must be fluid to the extent that easy syringeability exists. It must be stable under the conditions of manufacture and storage and must be preserved against the contaminating action of microorganisms, such as bacteria and fungi.

The prevention of the action of microorganisms can be brought about by various antibacterial and antifungal agents, for example, parabens, chlorobutanol, phenol, sorbic acid, thimerosal, and the like. In many cases, it will be preferable to include isotonic agents, for example, sugars or sodium chloride. Prolonged absorption of the injectable compositions can be brought about by the use in the compositions of agents delaying absorption, for example, aluminum monostearate and gelatin.

Sterile injectable solutions are prepared by incorporating the active compounds in the required amount in the appropriate solvent with various of the other ingredients enumerated above, as required, followed by filtered sterilization. Generally, dispersions are prepared by incorporating the various sterilized active ingredients into a sterile vehicle which contains the basic dispersion medium and the required other ingredients from those enumerated above.

In the case of sterile powders for the preparation of the sterile injectable solutions, the preferred method of preparation are vacuum-drying and freeze drying techniques which yield a powder of the active ingredient plus any additional desired ingredient from a previously sterile-filtered solution thereof.

The pharmaceutical compositions of the invention generally comprise a buffering agent, an agent which adjusts the osmolarity thereof, and optionally, one or more pharmaceutically acceptable carriers, excipients and/or additives as known in the art. Supplementary active ingredients can also be incorporated into the compositions. The carrier can be solvent or dispersion medium containing, for example, water, ethanol, polyol (for example, glycerol, propylene glycol, and liquid polyethylene glycol, and the like), suitable mixtures thereof and vegetable oils. The proper fluidity can be maintained, for example, by the use of a coating, such as lecithin, by the maintenance of the required particle size in the case of dispersion and by the use of surfactants.

Local administration to the area in need of treatment is also included and may be achieved by, for example, local infusion during surgery, topical application, direct injection into the inflamed joint, directly onto the eye, etc.

For oral administration, the pharmaceutical preparation may be in liquid form, for example, solutions, syrups or suspensions, or in solid form as tablets, capsules and the like. For administration by inhalation, the compositions are conveniently delivered in the form of drops or aerosol sprays. For administration by injection, as indicated above, the formulations may be presented in unit dosage form, e.g., in ampoules or in multi-dose containers with an added preservative.

The compositions of the invention can also be delivered in a vesicle, for example, in liposomes. In another embodiment, the compositions can be delivered in a controlled release system.

The amount of the therapeutic or pharmaceutical composition of the invention which is effective in the treatment of a particular disease, condition or disorder will depend on the nature of the disease, condition or disorder and can be determined by standard clinical techniques. In addition, in vitro assays as well in vivo experiments may optionally be employed to help identify optimal dosage ranges. The precise dose to be employed in the formulation will also depend on the route of administration, and the seriousness of the disease, condition or disorder, and should be decided according to the judgment of the practitioner and each patients circumstances. Effective doses may be extrapolated from dose-response curves derived from in vitro or animal model test systems.

Disclosed and described, it is to be understood that this invention is not limited to the particular examples, methods steps, and compositions disclosed herein as such methods steps and compositions may vary somewhat. It is also to be understood that the terminology used herein is used for the purpose of describing particular embodiments only and not intended to be limiting since the scope of the present invention will be limited only by the appended claims and equivalents thereof.

It must be noted that, as used in this specification and the appended claims, the singular forms "a", an and "the" include plural referents unless the content clearly dictates otherwise.

Throughout this specification and the Examples and claims which follow, unless the context requires otherwise, the word "comprise", and variations such as "comprises" and "comprising", will be understood to imply the inclusion of a stated integer or step or group of integers or steps but not the exclusion of any other integer or step or group of integers or steps.

The following examples are representative of techniques employed by the inventors in carrying out aspects of the present invention. It should be appreciated that while these techniques are exemplary of preferred embodiments for the practice of the invention, those of skill in the art, in light of the present disclosure, will recognize that numerous modifications can be made without departing from the spirit and intended scope of the invention.

Materials & Methods

NKT Lymphocyte and Dendritic Cell Isolation

Donor mice were sacrificed at day 1 of the experiment and splenic lymphocytes were isolated and red blood cells removed as previously described [Trop, S. et al., Hepatology 29(3):746-55 (1999)]. Spleens were crushed through a stainless mesh (size 60, Sigma Chemical Co., St. Louis Mo.). Cell suspension was placed in a 50 ml tube for 3 minutes and washed twice in cold PBS (1,250 rpm for 10 minutes), and debris removed. Cells were re-suspended in PBS, and placed through a nylon mesh presoaked in PBS, and unbound cells were collected. Cells were washed twice in 45 ml PBS (1,250 rpm at room temperature). The viability by trypan blue staining was expected to be more than 95%. Cell separation was performed using Magnetic Cell Sorting (MACS). NKT cells were isolated using both anti CD3 and anti-NK1.1 beads, while dendritic cells were isolated using anti CD11a beads, in accordance with the manufacturer's instructions (Miltenyl Biotec, Bergisch Gladbach, Germany).

Flow Cytometry Analysis for Determination of Natural Killer Cell Population

Following natural killer cell isolation, triplicates of $2-5 \times 10^5$ cells/500 µl PBS were put into Falcon 2052 tubes incubated with 4 ml of 1% BAS for 10 minutes, and centrifuged at 1400 rpm for 5 minutes. Cells were resuspended in 10 µl FCS with 1:20 CY5-conjugated CD45 antibody and PE-conjugated anti-pan NK antibody (eBioscience, USA), and mixed every 10 minutes for 30 minutes. Cells were washed twice in 1% BSA, and kept in 4° C. unitl reading. For the control group, only 5 µl of 1% BSA was added. Analytical cell sorting was performed on $1 \times 10^4$ cells from each group with a fluorescence-activated cell sorter (FACSTAR plus, Becton Dickinson). Only live cells were counted, and background fluorescence from non-antibody-treated lymphocytes was deducted from the levels obtained. Gates were set on forward- and side-scatters to exclude dead cells and red blood cells. The data was analyzed with Consort 30 two-color contour plot program (Becton Dickinson, Oxnard, Calif.), using the CELLQuest program.

HCC Cell Culture

Mouse hepatoma cell line HEPA 1-6 (CRL 1830), was grown in culture as monolayers in a medium supplemented with nonessential aminoacids and 10% heat inactivated fetal bovine serum.

The human Hepa 3B hepatocellular carcinoma cell line was obtained from American type culture collection (ATCC), VA. Cell were grown as monolayers in cultures containing DMEM medium, supplemented with 10% heat-inactivated fetal bovine serum, 1% L-glutamine, nonessential amino acids, penicillin and streptomycin.

Preparation of HCC Lysate $0.4 \times 10^6$ HEPA 1-6 or HEP-3B cells were separated, placed in Eppendorf tubes, and centrifuged at 250 g for 5 minutes. The pellet was separated and subjected to three cycles of freeze-thaw in liquid nitrogen. Protein quantification was performed using commercial kits, following manufacturer's instructions.

NKT Proliferation Using Radioactive Thymidine Incorporation

Isolated NKT lymphocytes and dendritic cells were cultured in microwell plates (Sterilin Co.), with or without HCC related antigens and elevated doses of leptin, in a total volume of 0.2 ml RPMI 1640 culture medium, supplemented with 100 mg/ml penicillin, 100 mg/ml streptomycin, 2 mM L-glutamine, with $5 \times 10^{-5}$ M 2ME, and 10% FCS. After 24 h in a 37° C. humidified 5% $CO_2$ incubator, 1 mmCi of $^3$H TdR (5 Ci/nmol, Nuclear Research Center, Negev, Israel) was added to each well. Cells were collected 16 h later on paper filters, using a multiple sample harvester (Titertek Cell Harvester 530; Flow Laboratories, McClean, Va.). Radioactivity was measured by a liquid scintillation counter. Background results were subtracted.

Cytokine Measurement

The content of each plate was centrifuged and the supernatant fluid was collected. Supernatant cytokine levels (and serum cytokine levels, including leptin, IL10, IL12, IL4, TNF-x, and TGF-β) were measured by a "sandwich" ELISA method, using Genzyme Diagnostic kits (Genzyme Diagnostics, Mass., USA) according to the manufacturer's instructions.

STAT and SMAD Western Blot Analysis

Expression of the transcription factors STAT (signal transducer and activator of transcription) 1, 3, 4 and 6, p-STAT 1, 3, 4, 6, and SMAD and p-SMAD 1-4 in splenocytes was determined by Western blot analysis of protein extraction of splenocytes from each plate. Splenocytes were lysed in 100 µl of lysis solution (Sigma). Proteins (100 µg/lane) were resolved by electrophoresis on SDS-polyacrylamide (7.5%) gels, and electroblotted to nitrocellulose membranes (Schleicher & Scuell, Germany). Probing with a polyclonal rabbit anti-mouse antibody for the different tested STAT and SMAD proteins (Santa Cruz Biotechnology) was followed by addition of horseradish peroxidaseconjugated goat anti-rabbit IgG (Jackson Immuno Research, PA, USA).

Determination of the Presence of Leptin Receptors on NKT Cells

NKT cells were cultured on six well plates, and were washed and lysed in lysis buffer. Spleens were crushed through a stainless mesh (size 60, Sigma Chemical Co., St Louis Mo.). Cell suspension was placed in a 50 ml tube for 3 minutes and washed twice in cold PBS (1,250 rpm for 10 minutes), and debris was removed. Cells were re-suspended in PBS, and placed through a nylon mesh presoaked in PBS, and unbound cells were collected. Cells were washed twice in 45 ml PBS (1,250 rpm at room temperature). For splenocyte isolation, 20 ml of histopaque 1077 (Sigma Diagnostics, St. Louis, Mo.) was slowly placed underneath the cells suspended in 7 ml of PBS, in a 50-ml tube. The tube was centrifuged at 1,640 rpm for 15 minutes at room temperature. Cells at the interface were collected, diluted in a 50-ml tube, and washed twice with ice-cold PBS (1,250 rpm for 10 minutes). The viability by trypan blue staining was more than 95%. Cell separation was performed using Magnetic Cell Sorting (MACS). For NKT cells, both anti CD3 and anti-NK1.1 were used (Miltenyl Biotec, Bergisch Gladbach, Germany).

Cell lysate was transferred to micro centrifuge tubes and clarified by centrifugation. The supernatant was collected and the protein content was determined by a BCA protein assay kit for Western blotting analysis, equal amounts of protein were separated by sodium dodecyl sulfate (SDS) polyacrylamide gel electrophoresis [8%] and were transferred onto a nitrocellulose membrane. The membrane was immuno-blotted with goat anti-leptin receptor antibodies (Santa Cruz, USA).

Mice Groups 8-week old male nude mice, SCID mice, and SCID-beige mice were purchased from Jackson Laboratories (Bar Harbor, Me.). All animals were housed in laminar flow hoods in sterilized cages, given irradiated food and sterile acidified water, and kept on regular 12 hour light-dark cycles. Food and water were administered ad libitum. Mice were weighed and food intake was recorded every two days. Mice were sacrificed on day 30 of the experiment by cervical dislocation, under isoflurane anesthesia. All animal experiments were carried out in accordance with the guidelines of the Hebrew University-Hadassah Instituional Committee for care and use of laboratory animals and with the committee's approval. Mice that showed signs of distress, lost 10% of body weight between measurements, or more than 25% of their initial body weight, were sacrificed.

Induction of HCC $1 \times 10^8$ HCC cells (of HEPA 1-6 origin) were injected intraperitoneally into wildtype c57bl and leptin-deficient ob/ob mice in order to determine the effect of leptin on HCC growth in these mice. Monitoring of tumor growth was performed weekly by mouse weighing and determination of tumor diameter by calipers. Any mouse that featured a loss of over 20% in body weight, exhibited signs of distress, or had an estimated tumor size of more than 15% of animal weight, was sacrificed.

Leptin Administration

Recombinant mouse leptin was purchased from R&D Co, and dissolved according to manufacturer's instructions. Leptin was administered in two daily intraperitoneal injections, at a dose of 0.5 µg/gram body weight per injection, as illustrated in Table 3 (see Example 2).

Pathological Examination

Hematoxylin/eosin staining of paraffin-embedded liver and tumor sections was performed. Sections were examined by two experienced pathologists, blinded to the criteria of the experiment.

Splenic and Hepatic Lymphocyte Isolation

Splenocytes were isolated and red blood cells removed as previously described [Shibolet, O. et al., J Leukoc Biol. 75(1):76-86 (2003)]. Intrahepatic lymphocytes were isolated from all groups of mice at the end of the study. The inferior vena cava was cut above the diaphragm and the liver was flushed with 5 ml of cold PBS until it became pale. The connective tissue and gall bladder were removed, and livers were placed in a 10-ml dish in cold sterile PBS. Livers and spleens were crushed through a stainless mesh (size 60, Sigma Chemical Co., St. Louis Mo.). Cell suspension was placed in a 50-ml tube for 3 minutes and washed twice in cold PBS (1,250×rpm for 10 minutes), and debris was removed. Cells were re-suspended in PBS, cell suspension was placed through a nylon mesh presoaked in PBS, and unbound cells were collected. Cells were washed twice in 45 ml PBS (1,250×rpm in room temperature). For liver and spleen lymphocyte isolation 20 ml of histopague 1077 (Sigma Diagnostics, St. Louis, Mo.) was slowly placed underneath the cells suspended in 7 ml of PBS, in a 50-ml tube. The tube was centrifuge at 1,640 rpm for 15 minutes at room temperature. Cells at the interface were collected, diluted in a 50-ml tube, and washed twice with ice-cold PBS (1,250 rpm for 10 minutes). Approximately $1 \times 10^6$ cells/mouse liver were recovered. The viability by trypan blue staining was expected to be more than 95%.

Flow Cytometry Analysis for Determination of Lymphocyte Subpopulations

Immediately following lymphocyte isolation, triplicates of $2-5 \times 10^4$ cells/500 µl PBS were put into Falcon 2052 tubes incubated with 4 ml of 1% BSA for 10 minutes, and centrifuged at 1400 rpm for 5 minutes. Cells were resuspended in 10 µl FCS with 1:20 FITC-anti mouse NK1.1 antibody (NKR-P1C, Pharmingen, USA), and mixed every 10 minutes for 30 minutes. Cells were washed twice in 1% BSA, and kept at 4° C. until reading. For the control group, only 5 µl of 1% BSA were added. Analytical cell sorting was performed on $1 \times 10^4$ cells from each group with a fluorescence-activated cell sorter (FACSTAR plus, Becton Dickinson). Only live cells were counted, and background fluorescence from non-antibody-treated lymphocytes was deducted from the levels obtained. Gates were set on forward- and side-scatters to exclude dead cells and red blood cells. The data was analyzed with Consort 30 two-color contour plot program (Becton Dickinson, Oxnard, Calif.), or the CELLQuest program.

Lymphocyte RNA Isolation and Semi-quantitative rtPCR

Total RNA from $10 \times 10^6$ splenocytes of each mouse of each experimental group was isolated and transcribed into complementary DNA using Promega Reverse Transcriptase Kit (USA). PCR products were obtained after 35 cycles of amplification with an annealing temperature of 56-62 and visualized by ethidium bromide staining after agarose electrophoresis. RtPCR products were semiquantified by visual analysis after normalization against the Actin internal control. Primer sequences used for mouse target gene detection are depicted in table 2.

Natural Killer Cell Cytotoxicity Determination $10^3$ Natural killer cells were incubated for 4 hours with several concentrations of target YAC cells (NK:YAC ratio of 1:5 to 1:0.04) in the presence of 0, 0.01, 0.1, 1 mcg/ml mouse leptin. Cytotoxicity was determined by measuring lactate dehydrogenase (LDH) activity released in the media following 4 hours of incubation, using the CytoTox96 nonradioactive assay (Promega) and quantitated by measuring wavelength absorbance at 490 nm. Data were normalized to a maximal release of LDH upon lysis of YAC cells with (100%) and are corrected for spontaneous baseline LDH release from YAC cells, NK cells and the buffer.

Natural Killer Cell Proliferation Assay

Splenocytes were collected and prepared as described above. Natural killer cells were produced from splenocytes using double passage through magnetic beads conjugated to monoclonal hamster antimouse pan-NK antibody (Miltenyi Biotec, Bergisch Gladbach, Germany), in accordance with the manufacturer's instructions. Natural killer cells were seeded in RPMI medium containing 10% fetal calf serum at a density of $1 \times 10^4$ cells/16-mm well of a 24-well plate, in quadruplicates, in the presence of 500 ng/ml recombinant mouse IL-2. Each quadruplicate was added with 0, 0.01, 0.1, or 1 mcg/ml mouse highly purified leptin. After 5 days of incubation, methyl-$H^3$ thymidine was added to all wells (1 µCi/ml, Amersham Pharmacia Biotech, Little Chalfont, UK). Cell cultures were harvested following 16 hours. Data were given as mean stimulation indices of triplicates, expressed as counts per minute (CPM).

HCC Cell Proliferation

HEPA 3B Cells were cultured in DMEM medium containing 10% fetal calf serum at a density of $1 \times 10^3$ cells/16-mm well of 24-well plate, in quadruplicate, in the presence of 0, 0.01, 0.1, and 1 mcg/ml human highly purified leptin. After 5 days of incubation, methyl-$H^3$ thymidine was added to all wells (1 µCi/ml, Amersham Pharmacia Biotech, Little Chalfont, UK). HCC cell cultures were harvested following 16 hours. Data were given as mean stimulation indices of triplicates, expressed as counts per minute (CPM).

HCC Cell & Natural Killer Cell Proliferation Assay

Mouse natural killer cells wer isolated from splenocytes as described above. Natural killer cells were irradiated with 3000 rads prior to incubation to avoid proliferation. A combination of $1 \times 10^3$ HEPA 3B Cells and $1 \times 10^4$ mouse derived natural killer cells were cultured in RPMI medium containing 10% fetal calf serum and 500 ng/ml IL2 at a density of $1 \times 10^3$ cells/16-mm well of a 24-well plate, in quadruplicate, in the presence of 0, 0.01, 0.1, and 1 mcg/ml human highly purified leptin. After 5 days of incubation, methyl-$H^3$ thymidine was added to all wells (1 µCi/ml, Amersham Pharmacia Biotech, Little Chalfont, UK). HCC cell cultures were harvested following 16 hours. Data were given as mean stimulation indices of triplicates, expressed as counts per minute (CPM).

HCC Cell mRNA Determination

HEPA 3B Cells were cultured in quadruplicates for 1, 2, and 6 hours in RPMI medium containing 10% fetal calf serum at a density of $1\times10^6$ cells/16-mm well of a 24-well plate, in the presence of 0.5 mcg/ml, 5 mcg/ml, 50 mcg/ml human highly purified leptin. Total RNA was isolated and transcribed into complementary DNA using Promega Reverse Transcriptase Kit (USA). PCR products were obtained after 35 cycles of amplification with an annealing temperature of 56-62 and visualized by ethidium bromide staining after agarose electrophoresis. RtPCR products were semiquantified by visual analysis after normalization against the Actin internal control. Primer sequences used for mouse target gene detection are depicted in table 3.

In vitro Lymphocyte Incubation $1\times10^5$ splenic lymphocytes from each mouse were cultured in 96-well plates in the presence of concanavalin A (used here as a T lymphocyte activator), for 24 hours. Subsequently, plates were centrifuged and the supernatant fluid removed. Determination of supernatant levels of IFN-g, IL10, 1L12 was performed using 'sandwich ELISA' (described above).

HCC in T Cell Deficient Mice

The above experiments were repeated in T cell deficient nude mice. $1\times10^7$ HEP-3B HCC cells were injected subcutaneously, with or without the addition of leptin, as outlined in Table 1 below. Follow-up parameters were identical to the ones described above.

TABLE 1

In vivo nude mice experimental groups (n = 10)

| | |
|---|---|
| Group A | Ten-week-old male nude mice + HCC + 1 µg/g/day leptin |
| Group B | Ten-week-old male nude mice + HCC |
| Group C | Ten-week-old male nude mice + 1 µg/g/day leptin |
| Group D | Ten-week-old male C57BL/6 mice |

EXAMPLES

Example 1

In-vitro Addition of Increasing Doses of Leptin Results in Enhanced APC-dependent NKT Lymphocyte Proliferation In order to assert the immunomodulatory effects of leptin on regulatory cell (NKT and dendritic cell) proliferation and cytokine secretion profile, the inventors have performed a series of in-vitro experiments assessing the effect of leptin on NKT lymphocyte proliferation, particularly in the presence of HCC related antigens. NKT cells were harvested from wild-type c57bl mice using double beading techniques (anti-CD3+ anti-NK1.1 & anti-CD11a, for NKT and dendritic cells, respectively), as described in Experimental Procedures. Triplicates of $1\times10^5$ NKT cells were either incubated alone, or with the addition of $1\times10^4$ dendritic cells (DC). A crude lisate of HEPA 1-6 HCC cells (made out from $5\times10^6$ cells), and increasing doses of leptin were added to each plate, as indicated in Table 2, which lists all experimental groups. The same experiment was later repeated using a human HEP-3B HCC lysate, in order to determine whether the same response occurs in the presence of human HCC antigens.

Figure 1:
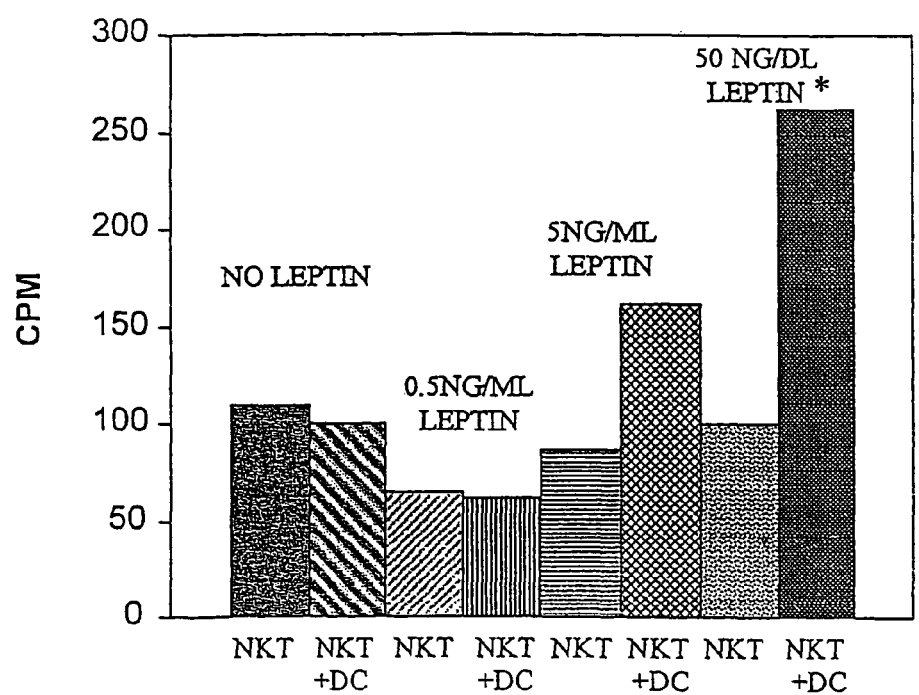
FIG. 1 Leptin induces in-vitro proliferation of NKT cells

Plates were incubated for one day, and NKT cell proliferation was determined using thymidine uptake techniques. As shown by FIG. 1, higher doses of leptin resulted in greater NKT cell proliferation, in particularly in plates where NKT cells were incubated together with DC's (270 CPM, P<0.05). These results indicate that incubation of NKT cells with escalating doses of leptin, in the presence of tumor related antigens, results in increased NKT proliferation, when these cells are incubated together with dendritic cells. This suggests that leptin features a direct, dose-dependent, pro-proliferative influence on NKT cells, through activation of DC's.

TABLE 2

Experimental groups (triplicates)

| Group | Cells | Leptin | HCC antigens |
|---|---|---|---|
| Group A | NKT cell | No leptin | $5 \times 10^6$ HEP 1-6 cell lysate |
| Group B | NKT cell + DC | No leptin | $5 \times 10^6$ HEP 1-6 cell lysate |
| Group C | NKT cell | 0.5 ng/ml leptin | $5 \times 10^6$ HEP 1-6 cell lysate |

Example 2

Leptin Leads to Induction of HCC in T Cell Deficient Nude Mice which Results in a Substantial Increment in Tumor Growth In vitro and in vivo experiments were next performed in order to determine the presence of leptin receptors on HCC cells grown in cell culture. Since it was previously found that enhancement of tumor cell growth by leptin occurs through activation of the JAK/STAT pathway, the inventors further examined the effect of leptin addition on expression of STAT and STAT intracellular proteins. It should be noted that in vitro, leptin receptor mRNA expression and leptin-induced expression of signal transducer and activators (STAT) 1-6, suppressor of cytokine signaling (SOCS) 1-4, and cytokine-inducible S—H protein (C15) were determined in human HEPA-3B HCC cells. Subsequently, HCC was induced in leptin-deficient ob/ob mice [Schwartz, J. et al., Clin. Invest. 98(5):1101-6 (1996)] and their lean littermates, with or without the addition of leptin, as illustrated in Table 3, and the effect of leptin and leptin deficiency on HCC growth was determined. To analyze the direct and immune-mediated effects of leptin, HCC was induced as control in T cell deficient nude mice, with or without the addition of exogenous leptin.

As shown by FIG. 2, Induction of HEP 3B human HCC in immune deficient nude mice resulted in a significant decrease in tumor growth (FIG. 2B) in the presence of leptin (although these tumors showed a large necrotic center), in comparison to mice that were not treated with leptin (FIG. 2A). It should be noted that changes were notable after only five weeks of follow-up.

TABLE 3

In vivo ob/ob experimental Eroups (n = 10)

| | |
|---|---|
| Group A | Ten-week-old male ob/ob mice + PBS |
| Group B | Ten-week-old male C57BL/6 mice + PBS |
| Group C | Ten-week-old male ob/ob mice + 1 µg/g/day leptin |
| Group D | Ten-week-old male C57BL/6 mice + 1 µg/g/day leptin |
| Group E | Ten-week-old male ob/ob mice + HCC + PBS |
| Group F | Ten-week-old male C57BL/6 mice + HCC + PBS |
| Group G | Ten-week-old male ob/ob mice + HCC + 1 µg/g/day leptin |
| Group H | Ten-week-old male C57BL/6 mice + HCC + 1 µg/g/day leptin |

A comparative experiment, in which tumors of mice treated with leptin and mice which were not treated with leptin, is demonstrated by FIG. 3. As shown by the figure, tumors of mice that were treated with leptin (top row) were significantly smaller then tumors taken from mice which were not treated with leptin (bottom row).

However, histological evaluation of excised tumors of both groups (FIG. 3), clearly demonstrated that mice treated with leptin uniformly developed an intense inflammatory response in tumor interphase areas (FIG. 3B), whereas tumors of mice which were not treated with leptin, showed no inflammatory response.

These results clearly demonstrate the feasibility of the use of leptin for decreasing tumor size, and indicate that reduction of tumor size by leptin may be a result of an immuno-modulatory effect of leptin on induction of a pro-inflammatory response.

Example 3

Leptin Induces a Potent Pro-inflammatory Immune Response in the Concanavalin A Hepatic Damage Model To assess the immunomodulatory role of leptin on NKT cell dependent hepatic disease, the effect of leptin was assessed in the concanavalin A-induced hepatitis model [Watanabe, Y. et al., Hepatology 24(3):702-10 (1996)]. Wildtype c57bl/6 mice were divided into 4 groups, as shown in Table 4. Group A and C mice were administered with two daily intraperitoneal injections of 0.5 mg/g body weight leptin for one week. On day eight, mice of groups A and B were intravenously administered with 20 mg/g concanavalin A (conA). Eight hours later all mice were sacrificed.

Leptin administration resulted in significantly exacerbated concanavalin-induced hepatitis. Group A mice featured significantly elevated serum ALT activity (4578±2226 u/l, FIG. 5) in comparison to group B mice (2035±446 u/l, P<0.05). Hepatic histology from group A mice demonstrated significantly increased hepatic necrosis and inflammation as compared to group B mice (FIG. 6). The administration of leptin without the induction of concanavalin A hepatitis did not in itself result in elevated ALT (alanine amino transferase) levels (114±101 u/l) or hepatic necrosis (FIGS. 5 and 6, respectively).

TABLE 4

| Preliminary experiment B groups (N + 10) | | |
|---|---|---|
| Group | Leptin | Concanavalin A |
| Group A | + | + |
| Group B | − | − |
| Group C | + | + |
| Group D | − | − |

In vitro exposure to concanavalin A of cultured splenocytes from all mice groups at the end of the experiment resulted in a significant increase in the ratio of supernatant levels of IFN-γ/IL10 in group A mice that were treated with both leptin and Concanavalin A (0.6±0.5) as shown by FIG. 5, in comparison to mice of group B (0.17±0.1), C (0.32±0.08), and D (0.15±0.07, P=0.07). Hepatic NKT lymphocytes were significantly lower among group A mice (4±1.2%), in comparison to group B (10±0%), C (12±8%) & D (30±8.5%), possibly reflecting the activation-induced apoptosis.

These results suggest that leptin functions as a pro-inflammatory immune modulating agent, inducing exacerbation of Th1 immune response, pro-inflammatory cytokine secretion, possibly through NKT lymphocyte activation.

Example 4

In-vivo Effect of Leptin Administration on Hepatocellular Carcinoma in Athymic Mice Leptin administration resulted in a significant inhibition of hepatocellular carcinoma growth and improved survival in athymic mice. Differences in tumor size between leptin-administered and saline-administered mice were noted after two weeks of tumor implantation. After six weeks of follow-up, mean tumor volume in leptin-administered mice (1.04±0.12 cm$^3$) was significantly lower than in saline-administered mice (1.9±0.9 cm$^3$, P<0.001, FIG. 3). Mean tumor weight was significantly lower in leptin-administered mice (0.31±0.05 grams) as compared to saline administered mice (0.63±0.37gr, P=0.002). Mortality was significantly lower among leptin-administered than among saline-administered mice (0% vs. 20% mortality on week 6, respectively, P<0.0001).

Macroscopically, tumors of leptin-administered mice featured a small solid mass and a large necrotic center, whereas tumors in saline-administered mice were composed of a much larger solid mass and a significantly smaller area of necrosis (FIG. 9). Microscopically, tumors in leptin-administered mice featured a dense inflammatory infiltrate, mainly in the interphase area. The inflammatory exudates was composed of a mixture of lymphocytes and neutrophilles (FIG. 8). Such intra-tumor infiltrate was not notable in saline-administered mice. Leptin-administered and saline-administered mice in control groups B & D did not feature tumor growth or mortality.

Example 5

In-vivo Effect of Leptin Administration on Natural Killer Subsets

Peripheral natural-killer cell population was expanded in leptin-administered, HCC-implanted mice (6.16±2.19%) in comparison to saline administered mice (3.25±0.67%, P=0.03). A similar increase in NK cell population was noted in leptin-administered control group B as compared to saline-administered group D (1.27±2.73 vs. 0.58±0.37%, in groups B and D, respectively, P=0.007, FIG. 4). No statistically significant differences in the hepatic/splenic natural killer cell ratio were noted between leptin and saline administered mice (1.02±1.41, 0.45±0.64, 1.05±1.05, 0.25±0.24, for groups A-D respectively, P=NS).

Example 6

In-vivo Effect of Leptin Administration on Natural Killer Cell mRNA Expression

Semiquantitative rtPCR analyis of peripheral lymphocyte mRNA expression of several pro and anti-inflammatory factors revealed significantly decreased expression of CIS protein in leptin-administered as compared to saline administered mice (FIG. 9). Lymphocyte mRNA expression of STAT1-6, SOCS 1-4 did not differ between groups.

Example 7

In vivo Effect of Leptin Administration on Cytokine Profile

Serum leptin levels were significantly higher in leptin treated group A and B mice (7.05 ng/ml and 6.29 ng/ml, respectively) than saline treated group C and D mice (3.24 ng/ml and 1.57 ng/ml, respectively, P<0.01). No significant difference between groups was noted in any of the other serum cytokine levels (P=NS).

Example 8

In-vivo Effect of Leptin Administration on Hepatocellular Carcinoma in SCID and in SCID-Beige Mice To further determine the role of natural killer cells in leptin-associated tumor suppression, the in-vivo experiments were repeated using T&B cell deficient SCID mice and T, B & natural killer cell deficient SCID-Beige mice. Leptin administration to SCID mice resulted in similar tumor inhibition to that observed in Athymic nude mice. Numbers. In natural killer cell-deficient SCID beige mice, on the other hand, tumor volume and tumor weight were significantly larger (5.05±2.65 cm$^3$ & 2.73±1.61 grams in SCID-Beige saline administered mice compared to 1.9±0.9 cm$^3$ & 0.63±0.37 grams in saline-administered nude mice, p<0.001 for both parameters). Leptin and saline-administered SCID Beige mice suffered of 30% & 40% mortality, respectively, throughout the experimental period. In contrast to nude and SCID mice, leptin-administration to SCID-beige mice resulted in no tumor inhibitory effect (mean tumor volume of 4.62±2.29 cm$^3$ & weight of 2.12±0.8 grams in leptin-administered mice, P=NS for both parameters, (FIG. 3). Macroscopically, tumors in SCID beige mice, in leptin and saline-administered mice, featured no central areas of necrosis.

Example 9

In-vitro Effect of Leptin Administration on Natural Killer Cell Cytotoxicity

Leptin manifested a dose-dependent increase in natural killer cell cytotoxicity in vitro (FIG. 10). A 4 hour incubation of mouse-derived natural killer cells with YAC cells in the presence of increasing doses of mouse leptin (0.01 mcg/ml to 1 mcg/ml) resulted in a significantly increased natural-killer cell mediated lysis of YAC cells (manifested as increased LDH release). This leptin-medicated dose-response enhancement in cytotoxicity was notable in each of the tested NK-YAC ratios (5:1 to 0.04:1 NK-YAC ratios). In each NK-YAC ratio, cytotoxicity increased with increasing doses of leptin. In the highest tested NK-YAC ratio of 5:1, administration of 1 mcg/ml leptin resulted in a 100% 4-hour cytotoxicity.

Example 10

In-vitro Effect of Leptin Administration on Natural Killer Cell Proliferation

High dose leptin (1 mcg/ml) but not lower doses (0.1 & 0.01 mcg/ml) induced in vitro proliferation of natural killer cell. Incubation of 1×10$^4$ natural killer cells with 0, 0.01, and 0.1 mcg/ml mouse leptin resulted in thymidine uptake of 1361±143, 1302±173, and 1359±229 CPM, respectively, P=NS. Incubation with 1 mcg/ml leptin, on the other hand, resulted in a significantly elevated thymidine uptake of 2733±52 CPM. P<0.05

Example 11

In-vitro Effect of Leptin Administration on Hepatocellular Carcinoma Cell Proliferation In-vitro administration of leptin to HEPA 3B hepatocellular carcinoma cell culture resulted in a dose-dependent inhibition of tumor cell growth (FIG. 11). A 5-day incubation of 10$^3$ HCC cells in the presence of increasing leptin doses resulted in significant reduction in thymidine incorporation, from 7678±2603CPM in the absence of leptin to 3371±1178 CPM in the presence of 0.1 mcg/ml leptin, and 832±289 CPM in the presence of 1 mcg/ml leptin, P<0.001. Maximal inhibition was noted at 0.1 mcg/ml, with no added inhibition noted with the addition of 1 mcg/ml leptin (1287±412) as compared to 0.1 mcg/ml leptin (P=NS).

Example 12

In-vitro Effect of Leptin Administration Hepatocellular Carcinoma Proliferation in Presence of Natural Killer Cells The NK cell mediated effect of leptin on HCC cell proliferation was assessed by incubation of 10$^3$ HCC cells for 5 days in the presence of 10$^4$ irradiated natural killer cells in the presence of increasing leptin doses. Incubation of HCC cells in the presence of natural killer cells resulted in further inhibition of tumor cell growth, from 885±152 CPM without leptin, to 815±117 CPM, 724±44, & 613±95 CPM in the presence of 0.01, 0.1, and 1 mcg/ml leptin, respectively, (P<0.05 for 0.1 & 0.01 mcg/ml leptin).

Example 13

In-vitro Effect of Leptin Administration on Hepatoma Cell mRNA Expression

HEPA 3B cells expressed leptin receptor mRNA. To determine possible mechanisms by which leptin mediates its inhibitory affect on HCC cell growth, Hep3B cells were incubated in the presence of increasing leptin doses (0.5 mcg/ml, 5 mcg/ml, 50 mcg/ml for 45 minutes, 2 and 6 hours. Semi quantitative rtPCR demonstrated that leptin administration, even at the lowest doses, resulted in increased mRNA expression of STAT2 and SOCS1 in HCC cells (FIG. 12). Increased mRNA expression was notable after two hours for STAT2 and SOCS1. No effect of leptin administration on mRNA expression was noted for STAT 1 & 3-6, SOCS 2-4, and CIS.

The invention claimed is:

1. A method of treating cancer or an immune disorder caused by immune suppression in a subject comprising administration of a reagent that increases the activity of leptin in said subject wherein a shift takes place in the Th1/Th2 balance towards a pro-inflammatory state, wherein said cancer or said immune disorder is Hepatocellular carcinoma (HCC).

2. A method for the treatment of an immune-related disorder in a subject comprising increasing the activity of leptin in said subject by administering to said subject an immunomodulatory amount of leptin, any functional homologue, functional derivative, or functional fragment of leptin, or any combination of any of the foregoing, wherein said immune-related disorder is Hepatocellular carcinoma (HCC).

3. The method of claim 1 wherein increasing the activity in said subject comprises raising the amount of leptin in said subject.

4. The method of claim 3 wherein said increase in leptin amount is caused by administering to said subject an immunomodulatory amount of leptin, any functional homologue, functional derivative, or functional fragment of leptin, or any combination of any of the foregoing.

* * * * *